(12) United States Patent
Chun et al.

(10) Patent No.: US 11,781,180 B2
(45) Date of Patent: Oct. 10, 2023

(54) DETECTION OF ABNORMAL SIGNAL USING TWO OR MORE DATASETS

(71) Applicant: SEEGENE, INC., Seoul (KR)

(72) Inventors: Jong Yoon Chun, Seoul (KR); Mi Hyun Jang, Seoul (KR)

(73) Assignee: SEEGENE, INC., Seoul (KR)

( * ) Notice: Subject to any disclaimer, the term of this patent is extended or adjusted under 35 U.S.C. 154(b) by 1383 days.

(21) Appl. No.: 16/089,101

(22) PCT Filed: Mar. 31, 2017

(86) PCT No.: PCT/KR2017/003551
§ 371 (c)(1),
(2) Date: Sep. 27, 2018

(87) PCT Pub. No.: WO2017/171469
PCT Pub. Date: Oct. 5, 2017

(65) Prior Publication Data
US 2019/0284605 A1    Sep. 19, 2019

(30) Foreign Application Priority Data

Apr. 1, 2016 (KR) .................. 10-2016-0040390

(51) Int. Cl.
*G16B 30/00* (2019.01)
*C12Q 1/686* (2018.01)
*G16B 25/20* (2019.01)

(52) U.S. Cl.
CPC ............. *C12Q 1/686* (2013.01); *G16B 25/20* (2019.02); *G16B 30/00* (2019.02); *C12Q 2537/165* (2013.01)

(58) Field of Classification Search
CPC .......................... G16B 30/00; C12Q 2537/165
See application file for complete search history.

(56) References Cited

U.S. PATENT DOCUMENTS

| 2003/0125315 A1* | 7/2003 | Mjalli ................... C07C 271/22 514/210.01 |
| 2008/0154512 A1 | 6/2008 | Leong |
| 2011/0004411 A1 | 1/2011 | Paul et al. |
| 2014/0095136 A1 | 4/2014 | Oliphant et al. |
| 2015/0186598 A1 | 7/2015 | Chakrabarti et al. |

OTHER PUBLICATIONS

Quince, et al.; Removing noise from pyrosequenced amplicons; BMC Bioinformatics, vol. 12, Article No. 38 (internal pp. 1-18) (2011).

\* cited by examiner

*Primary Examiner* — Jamara A Franklin
(74) *Attorney, Agent, or Firm* — Gianna Julian Arnold; Saul Ewing LLP

(57) ABSTRACT

The present invention relates to a method for de-tecting an abnormal signal using two or more datasets. The present invention makes it possible to detect abnormal signals based on characteristics of abnormal signals commonly occurring in two or more datasets, which is effectively applied to datasets obtained by a multiplex PCR method.

19 Claims, 11 Drawing Sheets

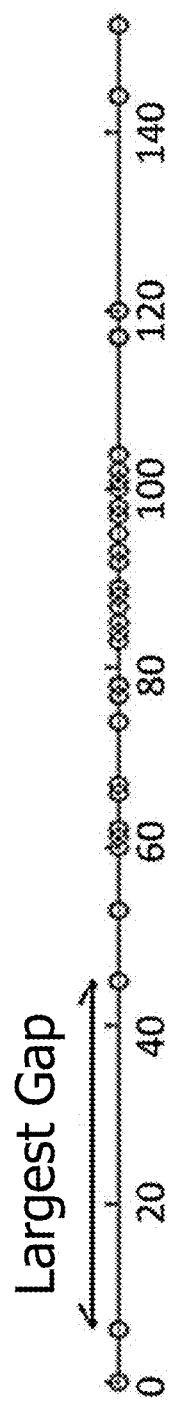

DETECTION OF ABNORMAL SIGNAL USING TWO OR MORE DATASETS

CROSS REFERENCE TO RELATED APPLICATIONS

This application claims priority and the benefit of PCT/KR2017/003551, filed Mar. 31, 2017, which claims priority and the benefit of KR 10-2016-0040390, filed Apr. 1, 2016, the entire contents of each of which are hereby incorporated in total by reference.

FIELD OF THE INVENTION

The present invention relates to detection of an abnormal signal using two or more datasets, particularly obtained by a signal amplification reaction in a single reaction vessel.

BACKGROUND OF THE INVENTION

For detection of target nucleic acid sequences through nucleic acid amplification, real-time detection methods are widely used to monitor target amplification in a real-time manner. Real-time PCR methods use a signal-generating means for releasing a detectable fluorescent signal in proportion to the amount of target nucleic acid sequence in a PCR reaction, so as to detect a particular target nucleic acid sequence. The release of the detectable fluorescence signal may be achieved, for example, by using an intercalator that emits a fluorescence signal upon bound to a duplex DNA, or an oligonucleotide containing both a reporter molecule and a quencher molecule of inhibiting the release of the fluorescence thereof.

The real-time PCR method measures a fluorescence signal proportional to the amount of target nucleic acid at each cycle, thereby generating a dataset including a plurality of data points, each data point having a pair of coordinate values of a cycle number and a signal intensity (signal value) at the cycle number. The dataset may be represented by an amplification curve (also referred to as an amplification profile curve or growth curve) where fluorescent intensity values are plotted vs. cycle numbers for convenience of data analysis. The dataset representing an amplification curve can then be analyzed to determine the presence or absence of a target nucleic acid sequence in a sample. For example, if there is a cycle having a fluorescent signal more than a threshold applied to the dataset representing an amplification curve, it can be determined that a target nucleic acid sequence is present in a sample.

For detection of a target nucleic acid sequence, it is essential to obtain an accurate and reliable dataset. However, despite elaborate experiments, the resulting datasets may contain abnormal signals (e.g., noises or errors) due to changes in annealing temperatures, the formation of air bubbles in reaction tubes or the presence of contaminant materials in samples. Examples of such abnormal signals include a sharp rise (also referred to as jump, spike and step) or decline (also referred to as dip) in fluorescence signals. The occurrence of such abnormal signals may lead to misinterpretation in qualitative or quantitative analysis of datasets, impairing the accuracy and reliability of the analysis.

Although there have been many attempts to prevent the occurrence of abnormal signals, its exact cause has not yet been clarified. Even if the exact cause is found, it is more difficult to prevent them in advance. Therefore, it would be more practical to analyze the dataset to determine whether abnormal signals have occurred, and if need, correct or invalidate it prior to determining the presence or absence of the target nucleic acid sequence from the dataset.

In this regard, some data analysis methods have been reported for identifying abnormal signals.

U.S. Pat. No. 8,560,247 discloses a technique for discriminating non-amplifying data, i.e., errors such as noise and jumps, which comprises receiving a set of data points, calculating a first function that approximates the set of data points, analyzing the first function to determine whether a slope of the first function exceeds a maximum amplification slope and if the maximum amplification slope is exceeded, identifying the exceeded slope segment as a non-amplifying segment of the curve. However, considering that a normal signal often exhibits amplification data exceeding the maximum amplification slope depending on the reaction conditions, the method is highly likely to determine a large number of normal signals as errors.

In addition, U.S. Patent Application Publication No. 2015/0186598 discloses a method for detecting jump errors based on determination of two consecutive cycles with different signs from a second derivative of a dataset. However, the method uses a threshold which is not so strict for determining a jump error, and the application of the threshold is complicated.

To our best knowledge, conventional approaches including the above-described methods employ a single dataset to identify abnormal signals, and have therefore limitations in terms of accuracy or utility of results.

Therefore, there remains a need to develop a novel analysis suitable for multiplex PCR methods, which can be used in determination of abnormal signals from multiple datasets in a more consistent and accurate manner.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

The present inventors have endeavored to improve conventional methods for detecting abnormal signals which may be found in datasets obtained by amplification reactions. As a result, the present inventors have developed a method for detecting abnormal signals using two or more datasets obtained by a signal amplification reaction in a single reaction vessel. In particular, the present inventors have established a new parameter, "normality score", which represents sign change between and magnitudes of the second-order change values at cycle numbers for the datasets, and have developed a novel method for detecting abnormal signals using the normality score.

Accordingly, it is an object of this invention to provide a method for detecting an abnormal signal using two or more datasets.

It is another object of this invention to provide a computer readable storage medium containing instructions to configure a processor to perform a method for detecting an abnormal signal using two or more datasets.

It is still another object of this invention to provide a device for detecting an abnormal signal using two or more datasets.

It is further object of this invention to provide a computer program to be stored on a computer readable storage medium to configure a processor to perform a method for detecting an abnormal signal using two or more datasets.

Other objects and advantages of the present invention will become apparent from the detailed description to follow taken in conjugation with the appended claims and drawings.

BRIEF DESCRIPTION OF THE DRAWINGS

FIG. 11 represents one-dimensional arrangement of total ranking scores (TRS) for the datasets (a)-(d) of FIG. 9, according to the magnitude of the TRS. In the arrangement, a reference TRS 0 is additionally inserted and the largest gap is indicated.

DETAILED DESCRIPTION OF THIS INVENTION

Figure 1:
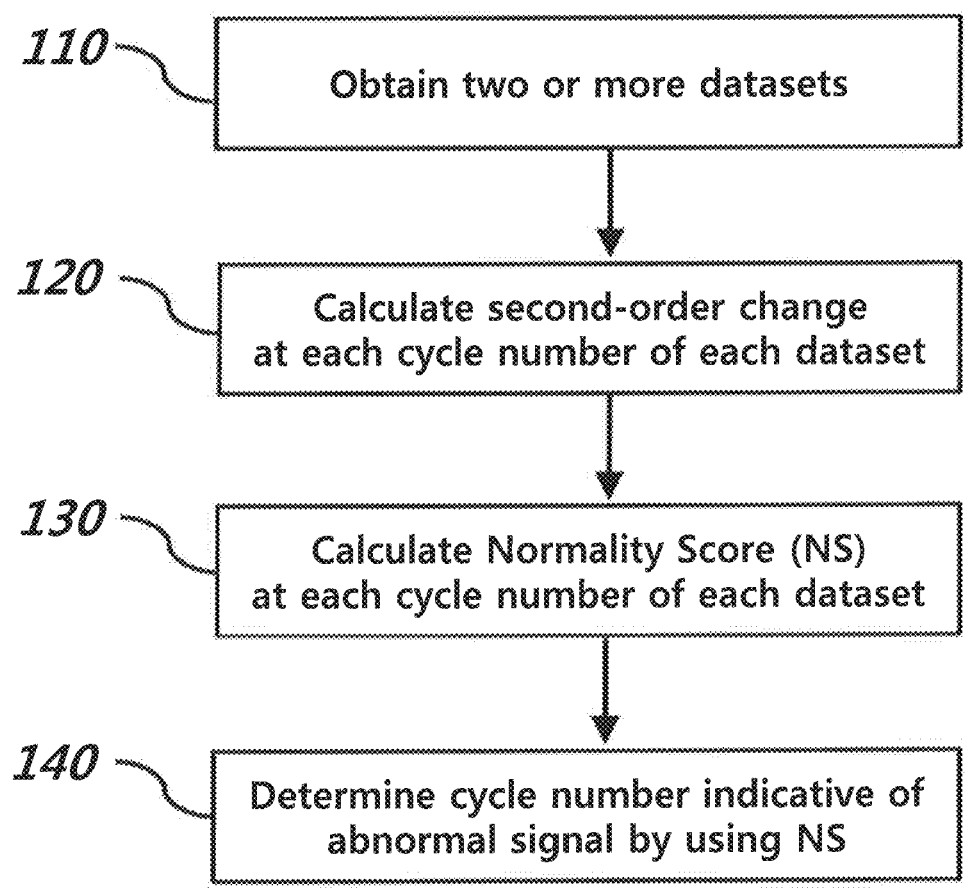
FIG. 1 is a flow chart representing a process for determining a cycle number indicative of an abnormal signal using two or more datasets in accordance with a representative embodiment of the present invention.

I. Detection of an Abnormal Signal Using Two or More Datasets

In one aspect of this invention, there is provided a method for detecting an abnormal signal using two or more datasets, comprising:

(a) obtaining two or more datasets by a signal amplification reaction in a single reaction vessel; wherein each of the datasets comprises a plurality of data points; wherein each of the data points has a cycle number and a signal value at the cycle number;

(b) calculating a second-order change value at each cycle number of each dataset;

(c) calculating a normality score at each cycle number of each dataset by using the second-order change value; wherein the calculation of the normality score is performed by a mathematical operation that represents sign change between and magnitudes of the second-order change values at two consecutive cycle numbers; and (d) determining a cycle number indicative of an abnormal signal by using the normality score.

The present inventors have endeavored to improve conventional methods for detecting abnormal signals which may be found in datasets obtained by a signal amplification reaction. As a result, the present inventors have developed a method for detecting abnormal signals using two or more datasets obtained by a signal amplification reaction in a single reaction vessel. In particular, the present inventors have established a new parameter, "normality score", which represents sign change between and magnitudes of the second-order change values at two consecutive cycle numbers for the datasets, and have developed a novel method for detecting abnormal signals using the normality score.

As used herein, the term "abnormal signal" refers to a signal which is not associated with an analyte (e.g., target nucleic acid sequence), i.e., a signal which is abruptly increased or decreased by other factors than an analyte during a signal amplification reaction. The term "abnormal signal" is used interchangeably with "error signal", "erroneous signal", "aberrant signal", "outlier signal" and "noise signal". The abnormal signal herein includes a signal indicating a sharp rise (e.g., jump, spike or step) or decline (e.g., dip) of the signal values in the amplification curve obtained from the signal amplification reaction. The causes of the abnormal signal include, but are not limited to, changes in annealing temperatures, the formation of air bubbles in reaction tubes or the presence of contaminant materials in samples.

The abnormal signal, if present, is likely to occur commonly in all datasets, particularly at a common cycle number or at adjacent cycle numbers, if the datasets are obtained by a reaction in a single vessel. Therefore, the present invention provides a method for analyzing two more datasets to identify abnormal signals which commonly occur among the datasets.

Also, if a particular cycle number indicates an abnormal signal in one dataset, the cycle number is also likely to indicate an abnormal signal in another dataset. Therefore, the present invention provides a method for analyzing one dataset to identify a cycle number indicative of an abnormal signal, and regarding the cycle number as a cycle number indicative of an abnormal signal for another dataset.

The present invention allows for the determination of abnormal signals in a flexible manner using two or more datasets.

An exemplary embodiment of the present method for determining a cycle number indicative of an abnormal signal using two or more datasets is illustrated in FIG. 1.

The present method will be described in more detail with reference to FIG. 1 as follows:

Step (a): Obtaining Two or More Datasets 110

In step (a), two or more datasets are obtained by a signal amplification reaction in a single reaction vessel. Each of the datasets includes a plurality of data points, each data point having a cycle number and a signal value at the cycle number.

Specifically, the two or more datasets are obtained by incubating a target analyte(s) in a sample with at least one signal-generating means in a single reaction vessel, and detecting signals by at least one detector.

The term "target analyte" as used herein encompasses a variety of materials (e.g., biological and non-biological materials), particularly biological materials, more particularly nucleic acid molecules (e.g., DNA and RNA), carbohydrates, lipids, amino acids, biological compounds, hormones, antibodies, antigens, metabolites and cells. Most particularly, the target analyte is a target nucleic acid molecule. The target analyte is present in a sample.

The term "sample" as used herein refers to any material undergoing the method of the present invention. Particularly, the term "sample" refers to any material containing or presumed to contain a nucleic acid of interest or which is itself a nucleic acid containing or presumed to contain a target nucleic acid sequence of interest. More particularly, the term "sample" as used herein includes biological samples (e.g., cells, tissues, and fluid from a biological source) and non-biological samples (e.g., food, water and soil). The biological samples includes, but not limited to, virus, bacteria, tissue, cell, blood, serum, plasma, lymph, sputum, swab, aspirate, bronchoalveolar lavage fluid, milk, urine, feces, ocular fluid, saliva, semen, brain extracts, spinal cord fluid (SCF), appendix, spleen and tonsillar tissue extracts, amniotic fluid and ascitic fluid. In addition, the sample may include natural-occurring nucleic acid molecules isolated from biological sources and synthetic nucleic acid molecules.

The term used herein "target nucleic acid", "target nucleic acid sequence" or "target sequence" refers to a nucleic acid sequence of interest for analysis, detection or quantification. The target nucleic acid sequence comprises a sequence in a single strand as well as in a double strand. The target nucleic acid sequence comprises a sequence newly generated in reactions as well as a sequence initially present in a sample.

The target nucleic acid sequence may include any DNA (gDNA and cDNA), RNA molecules and their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature.

The target nucleic acid sequence should not be construed as limiting the sequence known at a given time or the sequence available as of a given time, but instead should be read to encompass the sequence that may be available or known now or at any time in the future. In other words, the target nucleic acid sequence may or may not be known at the time of practicing the present method. In case of unknown target nucleic acid, its sequence may be determined by one of conventional sequencing methods prior to performing the present method.

When the target analyte is a target nucleic acid molecule, the sample may undergo a nucleic acid extraction procedure known in the art (see Sambrook, J. et al., Molecular Cloning, A Laboratory Manual, 3rd ed. Cold Spring Harbor Press (2001)). The nucleic acid extraction process may vary depending on the type of the sample. In addition, when the extracted nucleic acid is RNA, a reverse transcription process for synthesizing cDNA can be further performed (see Sambrook, J. et al., Molecular Cloning, A Laboratory Manual, 3rd ed., Cold Spring Harbor Press (2001)).

According to an embodiment of this invention, the target nucleic acid sequence comprises a nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term "nucleotide variation" used herein includes any variation at a particular location in a nucleic acid sequence. In other words, the term "nucleotide variation" includes a wild type and its any mutant type at a particular location in a nucleic acid sequence.

According to the present invention, the sample (or target analyte in the sample) is incubated with at least one signal-generating means in order to obtain signals for the target nucleic acid sequences.

The term "incubating," "incubate," or "incubation" as used herein refers to bring components together for their interaction or reaction. Particularly, the term refers to subjecting the components herein to a signal-generating process.

The term "signal-generating process" as used herein refers to any process capable of generating signals in a dependent manner on the properties of a target analyte in a sample, i.e., activity, amount or presence (or absence), particularly presence (or absence). The signal-generating process herein includes biological and chemical reactions. Such biological reactions include genetic analysis such as PCR, real-time PCR and microarray, immunological analysis and bacterial growth assays. According to an embodiment, the signal-generating process comprises analyzing the generation, change or destruction of the chemical substance.

The signal-generating process is accompanied with signal change. The signal change may serve as an indicator indicating qualitatively or quantitatively the presence or absence of a target nucleic acid sequence.

The details of "signal-generating process" are disclosed in WO 2015/147412 filed by the present inventors, the teachings of which are incorporated herein by reference in its entirety.

According to an embodiment, the signal-generating process is a signal amplification process.

According to an embodiment of this invention, the signal-generating process is a process with amplification or with no amplification of a target nucleic acid sequence.

Particularly, the signal-generating process is a process with amplification of a target nucleic acid molecule. More particularly, the signal-generating process is a process with amplification of a target nucleic acid molecule and capable of increasing or decreasing signals (particularly, increasing signals) upon amplifying the target nucleic acid molecule.

The term used herein "signal generation" include appearance or disappearance of signals and increase or decrease in signals. Particularly, the term "signal generation" means increase in signals.

The signal-generating process may be performed in accordance with a multitude of methods known to one of skill in the art. The methods include TaqMan™ probe method (U.S. Pat. No. 5,210,015), Molecular Beacon method (Tyagi et al., Nature Biotechnology, 14 (3):303 (1996)), Scorpion method (Whitcombe et al., Nature Biotechnology 17:804-807 (1999)), Sunrise or Amplifluor method (Nazarenko et al., Nucleic Acids Research, 25(12):2516-2521 (1997), and U.S. Pat. No. 6,117,635), Lux method (U.S. Pat. No. 7,537,886), CPT (Duck P, et al., Biotechniques, 9:142-148 (1990)), LNA method (U.S. Pat. No. 6,977,295), Plexor method (Sherrill C B, et al., Journal of the American Chemical Society, 126: 4550-4556 (2004)), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), Hybridization probe (Bernard P S, et al., Clin Chem 2000, 46, 147-148), PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (WO 2014/104818) and CER method (WO 2011/037306).

When the signal-generating process is performed in accordance with TaqMan™ probe method, the signal-generation means may comprise a primer pair, a probe with an interactive dual label and DNA polymerase having 5' to 3' nuclease activity. When the signal-generating process is performed in accordance with PTOCE method, the signal-generation means may comprise a primer pair, PTO (Probing and Tagging Oligonucleotide), CTO (Capturing and Templating Oligonucleotide) and DNA polymerase having 5' to 3' nuclease activity. Either PTO or CTO may be labeled with suitable labels.

According to an embodiment, the signal-generating process is performed in a process involving signal amplification together with target amplification.

According to an embodiment, the signal amplification reaction as the signal-generating process is performed in such a manner that signals are amplified simultaneously with amplification of the target nucleic acid sequence (e.g., real-time PCR). Alternatively, the signal amplification reaction is performed in such a manner that signals are amplified with no amplification of the target nucleic acid molecule [e.g., CPT method (Duck P, et al., Biotechniques, 9:142-148 (1990)), Invader assay (U.S. Pat. Nos. 6,358,691 and 6,194,149)].

A multitude of methods have been known for amplification of a target nucleic acid molecule, including, but not limited to, PCR (polymerase chain reaction), LCR (ligase chain reaction, see Wiedmann M, et al., "Ligase chain reaction (LCR)—overview and applications." PCR Methods and Applications 1994 February; 3(4):551-64), GLCR (gap filling LCR, see WO 90/01069, EP 439182 and WO 93/00447), Q-beta (Q-beta replicase amplification, see Cahill P, et al., Clin Chem., 37(9):1482-5 (1991), U.S. Pat. No. 5,556,751), SDA (strand displacement amplification, see G T Walker et al., Nucleic Acids Res. 20(7):16911696 (1992), EP 497272), NASBA (nucleic acid sequence-based amplification, see Compton, J. Nature 350(6313):912 (1991)), TMA (Transcription-Mediated Amplification, see Hofmann W P et al., J Clin Virol. 32(4):289-93 (2005); U.S. Pat. No. 5,888,779) or RCA (Rolling Circle Amplification, see Hutchison C. A. et al., Proc. Natl Acad. Sci. USA. 102:1733217336 (2005)).

The term "signal" as used herein refers to a measurable output. The term "signal value" as used herein is an expression that quantitatively represents a signal.

The magnitude, change, etc. of the signal may serve as an indicator indicating qualitatively or quantitatively the properties, particularly the presence or absence of a target analyte (a target nucleic acid sequence).

Examples of useful indicators include fluorescence intensity, luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The most widely used indicator is fluorescence intensity. The signal change includes generation or extinction of the signal as well as increase or decrease of the signal.

Signals include various signal characteristics from the signal detection, e.g., signal intensity [e.g., RFU (relative fluorescence unit) value or in the case of performing amplification, RFU values at a certain cycle number, at selected cycle numbers or at end-point], signal change shape (or pattern) or $C_t$ value, or values obtained by mathematically processing the characteristics.

According to an embodiment, the term "signal" includes not only signals per se obtained at detection temperatures but also a modified signal provided by mathematically processing the signals.

According to an embodiment of this invention, when an amplification curve is obtained by real-time PCR, various signal values (or characteristics) from the amplification curve may be selected and used for determination of target presence (intensity, $C_t$ value or amplification curve data).

The signal (particularly, the signal intensity) may vary depending upon its detection temperature as well as a signal-generating means employed.

The term "signal-generating means" as used herein refers to a means for providing a signal indicative of a property, specifically the presence or absence of a target analyte to be analyzed.

The term "signal-generating means" as used herein refers to any material used in generation of signals indicating the presence of target nucleic acid sequences, for example including oligonucleotides, labels and enzymes. Alternatively, the term used herein "signal-generating means" can be used to refer to any methods using the materials for signal generation.

A wide variety of the signal-generating means have been known to one of skill in the art. The signal-generating means include both labels per se and oligonucleotides with labels. The labels may include a fluorescent label, a luminescent label, a chemiluminescent label, an electrochemical label and a metal label. The label per se may serve as signal-generating means, for example, an intercalating dye. Alternatively, a single label or an interactive dual label containing a donor molecule and an acceptor molecule may be used as signal-generating means in the form of linkage to at least one oligonucleotide.

The signal-generating means may comprise additional components for generating signals such as nucleolytic enzymes (e.g., 5'-nucleases and 3'-nucleases).

The signal-generating means may comprises generating a signal in a dependent manner on the formation of a duplex; generating a signal using the formation of a duplex in a dependent manner on cleavage of a mediation oligonucleotide specifically hybridized to the target analyte; and generating a signal by cleavage of a detection oligonucleotide.

The term "signal amplification reaction" as used herein refers to a reaction that increases or decreases the signal generated by the signal-generating means.

According to an embodiment, the signal amplification reaction means a reaction that increases (amplifies) the signal generated by the signal-generating means depending upon the presence of a target analyte. This signal amplification reaction may or may not be accompanied with amplification of a target analyte (e.g., target nucleic acid molecule). Particularly, the signal amplification reaction means an amplification of the signal accompanied by amplification of a target analyte.

A dataset obtained by a signal amplification reaction includes cycle numbers.

The term "cycle number" or "cycle" as used herein refers to a unit of changes of conditions in a plurality of measurements accompanied with changes of conditions. For example, the changes of conditions include changes in temperature, reaction time, reaction number, concentration, pH and/or replication number of a target nucleic acid molecule sequence. Therefore, the cycle may include temperature, time or process cycle, unit operation cycle and reproductive cycle.

As one example, when a substrate decomposition capacity by an enzyme is analyzed depending on concentrations of the substrate, a plurality of measurements for the decomposition capacity by the enzyme is carried out with varying substrate concentrations. The increases in the substrate concentration may correspond to the changes of conditions and a unit of the increases may correspond to a cycle.

As another example, an isothermal amplification allows for a plurality of measurements for a sample in the course of reaction time under isothermal conditions and the reaction time may correspond to the changes of conditions and a unit of the reaction time may correspond to a cycle.

As still another example, in the case of the melting analysis or the hybridization analysis, the signal change may be measured as the temperature changes within a certain range of temperature, the temperature may correspond to the changes of conditions, and a unit of the temperature (e.g., measurement temperature) may correspond to a cycle.

More particularly, when repeating a series of reactions or repeating a reaction with a time interval, the term "cycle" refers to a unit of the repetition.

For example, in a polymerase chain reaction (PCR), a cycle refers to a reaction unit comprising denaturation of a target molecule, annealing (hybridization) between the target molecule and primers and primer extension. The increases in the repetition of reactions may correspond to the changes of conditions and a unit of the repetition may correspond to a cycle.

The dataset obtained by a signal amplification reaction include a plurality of data points, each data point having a cycle number and a signal value at the cycle number.

The term used herein "signal value" means either signal value actually measured at each cycle number of the signal-generating process (e.g., actual value of fluorescence intensity processed by signal amplification reaction) or its modification. The modification may include mathematically processed value of measured signal value (e.g., intensities). Examples of mathematically processed value of actually measured signal value (i.e., signal value of a raw dataset) may include, but are not limited to, a value obtained by adding a selected constant to the measured signal value, by subtracting a selected constant from the measured signal value, by multiplying the measured signal value by a selected constant, or by dividing the measured signal value by a selected constant; a logarithmic value of the measured signal value; or a derivative of the measured signal value. The term used herein "signal" is intended to encompass the term "signal value" and therefore these terms will be used interchangeably.

The signal value as used herein refers to a value obtained by absolutely or relatively quantifying the magnitude of a signal initially detected at the cycle number in the detector. The signal value is also referred to as a "zero-order signal value", a "raw signal value", or an "original signal value" in order to distinguish it from the first-order change value or the second-order change value. The unit of the signal value may vary depending on the type of signal generation reaction used. For example, when a signal value is obtained at each cycle number by a real-time PCR amplification reaction, the signal value may be represented by RFU (Relative Fluorescence Unit).

The term "data point" as used herein means a coordinate value comprising a cycle number and a signal value at the cycle number. The term "data" means all information that constitutes a dataset. For example, each of the cycle numbers and the signal values is a data.

Data points obtained by the signal-generating process, in particular the signal amplification reaction, can be represented as coordinate values in a two-dimensional rectangular coordinate system. In the coordinate values, the X-axis represents the cycle number, and the Y-axis represents the signal value measured or processed at the cycle number.

The term "dataset" as used herein refers to a set of data points. For example, the dataset may be a set of data points directly obtained by a signal amplification reaction performed in the presence of the signal-generating means, or it may be a set of data points modified from the original data points. The dataset may be all or part of a plurality of data points obtained by a signal amplification reaction or modified data points thereof.

The dataset may be plotted, giving an amplification curve.

As used herein, the term "amplification curve" refers to a curve obtained by a signal amplification reaction. The amplification curve includes a curve obtained in the presence of an analyte in a sample, or a curve (or line) obtained in the absence of an analyte in a sample.

According to one embodiment, the dataset used in the present invention is a raw dataset that has not undergone mathematical processing. According to another embodiment, the dataset used in the present invention is a mathematically processed dataset, for example a baseline-subtracted dataset, to remove background signals in a raw dataset. The baseline-subtracted dataset can be obtained by a variety of methods known in the art (e.g., U.S. Pat. No. 8,560,247).

According to one embodiment, the method of the present invention further comprises performing a signal-generating process (e.g., signal amplification reaction) to obtain datasets prior to the step (a).

One of the features of the present invention is to use two or more datasets obtained by a signal amplification reaction in a single reaction vessel. Unlike conventional techniques for detecting abnormal signals in a single dataset, the method of the present invention detects abnormal signals using two or more datasets obtained by a signal amplification reaction in a single reaction vessel, which is a unique aspect of the present invention.

Specifically, two or more datasets obtained by a signal amplification reaction in a single reaction vessel may be selected from two or more datasets obtained by detection at different detection temperatures, two or more datasets obtained by detection using different signal detection means, and a combination thereof.

The two or more datasets refer to datasets that are generated substantially simultaneously, for example the datasets generated during the reactions which start and end simultaneously in a single reaction vessel.

The datasets obtained by detection at different detection temperatures refers to dataset obtained, for example, by detecting changes in signal values at different detection temperatures (e.g., at least two detection temperatures at each cycle number) during a signal amplification reaction using a single signal-generating means in a single reaction vessel. For example, two or more datasets can be obtained from the signal amplification reaction by detection at different detection temperatures, according to the MuDT1 technology (WO 2015/147412) or the MuDT2 technology (WO 2016/093619) developed by the present inventor.

The datasets obtained by using different signal detection means refers to dataset obtained, for example, by detecting changes in signal values using different detecting means (e.g., optical modules) in a signal amplification reaction. For example, in a multiplex real-time PCR using two or more signal-generating means (e.g., fluorescent labels) for detection of two or more target nucleic acid sequences, datasets may be obtained by detecting signals from different signal-generating means using appropriate channels containing different optical modules. Further, the two or more datasets used in the present invention may be a combination of the datasets as described above. For example, the first dataset may be a dataset obtained using a signal-generating means "A" and at the relative high temperature detection temperature; the second dataset may be a dataset obtained using a signal-generating means "A" and at the relative low temperature detection temperature; the third dataset is a dataset obtained using a signal-generating means "B" and at the relative high temperature detection temperature and the fourth dataset is a dataset obtained using a signal-generating means "B" and at the relative low temperature detection temperature.

Step (b): Calculating a Second-Order Chancre Value at Each Cycle Number of Each Dataset 120

Afterwards, a second-order change value at each cycle number is calculated for each dataset by using the signal value at each cycle number. The calculation of the second-order change value in the step (b) is performed by calculating a first-order change value at each cycle number of each dataset by using two signal values at two consecutive cycle numbers, and then calculating a second-order change value at each cycle number of each dataset by using the two first-order change values at two consecutive cycle numbers.

In this step, a "first-order change value dataset" (including a plurality of data points having a cycle number and a first-order change value at the cycle number) and a "second-order change value dataset" (including a plurality of data points having a cycle number and a second-order change value at the cycle number) are obtained from a raw dataset (including a plurality of data points having a cycle number and a signal value at the cycle number) or a modified dataset thereof.

The term "signal value" as used herein is also referred to as a "zero-order signal value", "raw signal value", or "original signal value" in order to distinguish it from the value of the first-order change value or the second-order change value.

The term "change", "change value", or "value of change" as used herein in connection with the signal value at each cycle number means the quantity (or degree) of change of the signal value at a particular cycle number. The "$n^{th}$-order change value" as used herein means the quantity (or degree) of change in $(n-1)^{th}$-order change value at a particular cycle number. In particular, the zero-order change means a raw signal value. The term "change value" may be interchangeably used with the term "rate of change".

In this step, a second-order change value at each cycle number is obtained using a signal value at each cycle number. The second-order change value is obtained by calculating a first-order change value at each cycle number of each dataset by using two signal values at two consecutive (immediately adjacent) cycle numbers, and then calculating a second-order change at each cycle number of each dataset by using the two first-order change values at two consecutive (immediately adjacent) cycle numbers.

The change value may be any one selected from the group consisting of a difference, a difference quotient and a derivative, and thus the $n^{th}$-order change value (e.g., a first-order change value and a second-order change value) may be an $n^{th}$-order difference, an $n^{th}$-order difference quotient, or an $n^{th}$-order derivative.

The change value, in particular, a difference (difference value), a difference quotient (difference quotient value) and a derivative (derivative value), may be calculated or obtained by a number of methods known in the art.

For example, the difference as used herein may be obtained by calculating a difference between signal values at two immediately adjacent cycle numbers. The difference quotient as used herein may be obtained by dividing the difference by an interval between two immediately adjacent cycle numbers. The derivative as used herein may be obtained by subjecting signal values at 2, 3, 4, or more data points to a least squares method, or by determining the tangent line (slope) at each cycle number in an amplification curve.

The term "immediately adjacent cycle number" as used herein in connection with any particular cycle number refers to a cycle number that is contiguous to the particular cycle number, i.e., a cycle number that immediately precedes or immediately follows the particular cycle number. For example, in a typical dataset in which the cycle number increases by 1, the cycle number immediately adjacent to the $4^{th}$ cycle number is either the $3^{rd}$ cycle number or the $5^{th}$ cycle number.

In addition, the term "two immediately adjacent cycle numbers", "immediately adjacent two cycle numbers", or "consecutive cycle numbers" as used herein means two cycle numbers immediately adjacent to each other, i.e., two consecutive cycle numbers. For example, in a typical dataset in which the cycle number increases by 1, two immediately adjacent cycle numbers means cycle numbers x and x+1 or cycle numbers x−1 and x.

The symbols $y_i(x)$, $D_i(x)$, $D'_i(x)$ and $D''_i(x)$ used to calculate a second-order change value will have the following meanings:

The symbol $y_i(x)$ means a signal value at the $x^{th}$ cycle number of the $i^{th}$ dataset; $D'_i(x)$ means a first-order change value at the $x^{th}$ cycle number of the $i^{th}$ dataset; $D''_i(x)$ means a second-order change value at the $x^{th}$ cycle number of the $i^{th}$ dataset. In the above definition, i and x are each an integer of 1 or more. In particular, the integer i is used herein to denote a particular dataset among a plurality datasets. For example, when three datasets are obtained in the step (a), each of the datasets may be distinguished by use of the designations, such as $1^{st}$ dataset, $2^{nd}$ dataset and $3^{rd}$ dataset. Likewise, the integer x is used herein to denote a particular cycle number in a dataset. For example, when a dataset obtained consists of 45 cycle numbers, each of the cycle number may be distinguished by use of the designations, such as $1^{st}$ cycle number (cycle number 1), $2^{nd}$ cycle number (cycle number 2) ... $45^{th}$ cycle number (cycle number 45).

The second-order change value as used herein may be a second-order difference, a second-order difference quotient, or a second-order derivative.

The second-order difference may be obtained by calculating a first-order difference at each cycle number (including a plurality of data points having a cycle number and a first-order difference at the cycle number) by using two signal values at two immediately adjacent cycle numbers, and then calculating a second-order difference at each cycle number (including a plurality of data points having a cycle number and a second-order difference at the cycle number) by using two first-order differences at two immediately adjacent cycle numbers.

The second-order difference as used herein may be calculated in various ways known in the art.

In an embodiment, the second-order difference (or a second-order difference quotient) may be calculated by a forward difference method or a backward difference method known in the art.

According to the forward difference method, the second difference may be calculated by using the following Equations I and II sequentially or by using the following Equation III alone:

$$D'_i(x) = y_i(x+1) - y_i(x) \quad \text{Equation I}$$

$$D''_i(x) = D'_i(x+1) - D'_i(x) \quad \text{Equation II}$$

$$D''_i(X) = y_i(x+2) - 2*y_i(x+1) + y_i(x) \quad \text{Equation III}$$

According to the backward difference method, the second difference value may be calculated using the following Equations IV and V sequentially or by using the following Equation VI alone:

$$D'_i(x) = y_i(x) - y_i(x-1) \quad \text{Equation IV}$$

$$D''_i(x) = D'_i(x) - D'_i(x-1) \quad \text{Equation V}$$

$$D''_i(x) = y_i(x) - 2*y_i(x-1) + y_i(x-2) \quad \text{Equation VI}$$

For example, for the forward difference method, if $y_1(1)$, $y_1(2)$, $y_1(3)$, $y_1(4)$ and $y_1(5)$ are 1, 8, 30, 100 and 500, respectively, $D'_1(1)$, $D'_1(2)$, $D'_1(3)$ and $D'_1(4)$ will be 7 (=8−1), 22 (=30−8), 70 (=100−30) and 400 (=500−100), respectively, and $D''_1(1)$, $D''_1(2)$ and $D''_1(3)$ will be 15 (=22−7), 48 (=70−22) and 330 (=400−70), respectively; whereas, for the backward difference method, if $y_1(1)$, $y_1(2)$, $y_1(3)$, $y_1(4)$ and $y1(5)$ are 1, 8, 30, 100 and 500, respectively, $D'_1(2)$, $D'_1(3)$, $D'_1(4)$ and $D'_1(5)$ will be 7 (=8−1), 22 (=30−8), 70 (=100−30) and 400 (=500−100), respectively and $D''_1(3)$, $D''_1(4)$ and $D''_1(5)$ will be 15 (=22−7), 48 (=70−22) and 330 (=400−70), respectively.

It is noted that $D'_i(x)$ may be calculated by other equation, e.g., $D'_i(x) = y_i(x) - y_i(x+1)$ or $D'_i(x) = y_i(x-1) - y_i(x)$; and $D''_i(x)$ may be calculated by other equation $D''_i(x) = D'_i(x) - D'_i(x+1)$, $D''_i(x) = y_i(x) - 2*y_i(x+1) + y_i(x+2)$, $D''_i(x) = D'_i(x-1) - D'_i(x)$, or $D''_i(x) = y_i(x-2) - 2*y_i(x-1) + y_i(x)$.

In the forward difference method, both the end cycle number and the cycle number immediately before the end cycle number do not have $D''_i(x)$ calculated. For example, where the signal amplification reaction is performed up to 45 cycle numbers, $D''_i(45)$ and $D''_i(44)$ cannot be calculated due to absence of signal values at the $46^{th}$ cycle number or the $47^{th}$ cycle number.

Likewise, in the backward difference method, both the first cycle number and the cycle number immediately after the first cycle number (second cycle number) do not have $D''_i(x)$ calculated. For example, where the signal amplification reaction is performed up to 45 cycle numbers, $D''_i(1)$ and $D''_i(2)$ cannot be calculated due to absence of signal values at the $-1^{th}$ cycle number or the $0^{th}$ cycle number.

As such, the functions such as $y_i(x)$, $D_i(x)$, $D'_i(x)$ and $D''_i(x)$ are not calculated for a non-existing or undefinable cycle number.

It is noted that the results obtained by the forward difference method and the backward difference method have a certain interconvertibility with respect to cycle numbers.

Specifically, the $D''_i(x)$ obtained by the forward difference method is identical to the $D''_i(x+2)$ obtained by the backward difference method. For example, the second-order difference at the $1^{st}$ cycle number obtained by the forward difference method is the same as the second-order difference at the $3^{rd}$ cycle number obtained by the backward difference method.

Therefore, in view of such interconvertibility, one of skill in the art can readily convert the result of the forward difference method into the result of the backward difference method, or vice versa.

The calculation of the second-order differences by a backward difference method is illustrated in Examples of the present application. However, those skilled in the art can employ a forward difference method instead of the backward difference method such that only cycle numbers are altered to obtain the same result as the backward difference method. Alternatively, one skilled in the art can calculate second-order differences by a forward difference method, identify a cycle number indicative of an abnormal signal, and then alter the identified cycle number, thereby confirming a cycle number indicative of an abnormal signal.

Step (c): Calculating a Normality Score at Each Cycle Number 130

Next, in order to identify a cycle number(s) indicative of an abnormal signal for each dataset, a normality score is calculated at each cycle number of each dataset by using the second-order change value.

In this step, a "normality score dataset" including a plurality of data points having a cycle number and a normality score at a cycle number is obtained.

The calculation of the normality score is performed by a mathematical operation that represents sign change between and magnitudes of the second-order change values at two consecutive cycle numbers.

According to the present method, a cycle number(s) indicative of an abnormal signal is selected for each dataset, based on a normality score. According to the present invention, a small normality score indicates that the cycle number having the normality score is highly likely to exhibit an abnormal signal.

As used herein, the term "normality score" (abbreviated as NS) refers to a numerical value that represents both the sign change between the second-order change values at the two immediately adjacent cycle number and the magnitudes of the second-order change values at the two immediately adjacent cycle numbers. The normality score may be a numerical value representing the extent of normality of signals obtained by a signal amplification reaction. For example, a particular cycle number with a normality score of 1000 is likely to represent a normal signal, while another cycle number with a normality score of −2000 is likely to represent an abnormal signal.

The immediately adjacent cycle number used to calculate the normality score at the $x^{th}$ cycle number includes the cycle number immediately before or after the $x^{th}$ cycle number. For example, in a typical dataset in which the cycle number increases by 1, the immediately adjacent cycle number of the $x^{th}$ cycle number is the cycle number x+1 or cycle number x−1.

The normality score is obtained by a mathematical operation that represents sign change between and magnitudes of the second-order change values at two immediately adjacent cycle numbers. As described above, the second-order change value may be, for example, a second-order difference, a second-order difference quotient, or a second-order derivative.

According to an embodiment of the present invention, the normality score at the $x^{th}$ cycle number is calculated by a mathematical operation that represents sign change between and magnitudes of the second-order change values at the $x^{th}$ cycle number and the $(x+1)^{th}$ cycle number.

According to another embodiment of the present invention, the normality score at the $x^{th}$ cycle number is calculated by a mathematical operation that represents sign change between and magnitudes of the second-order change values at the $x^{th}$ cycle number and the second-order change value at the $(x-1)^{th}$ cycle number.

The sign change used herein indicates a circumstance where a second-order change value at the $x^{th}$ cycle number has a positive sign (positive value, +) and a second-order change value at the $(x+1)^{th}$ or $(x-1)^{th}$ cycle number has a negative sign (negative value, −). A mathematical operation that represents the sign change between the second-order change values is any operation that provides a negative normality score when a second-order change value at the $x^{th}$ cycle number has a positive sign and a second-order change value at the $(x+1)^{th}$ or $(x-1)^{th}$ cycle number has a negative sign; and provides a positive normality score when a second-order change value at the $x^{th}$ cycle number and a second-order change value at the $(x+1)^{th}$ or $(x-1)^{th}$ cycle number both have the same sign (e.g., all positive values or all negative values).

The magnitudes of the second-order change values as used herein indicate a combination of both the magnitude of the second-order change value at the $x^{th}$ cycle number and the magnitude of the second-order change value at the $(x+1)^{th}$ or $(x-1)^{th}$ cycle number.

Examples of the mathematical operation that represents sign change between and magnitudes of the second-order change values include a mathematical magnification (e.g., multiplication) of the second-order change values, a mathematical ratio (e.g., division) of the second-order change values, and the like.

According to one embodiment, the normality score is calculated by multiplying the second-order change values at the two immediately adjacent cycle numbers. The multiplication of the second-order change values can effectively represent sign change between and magnitudes of the second-order change values.

More specifically, the normality score may be calculated by the following Equation VII or VIII:

$$NS_i(x)=D''_i(x)*D''_i(x+1) \qquad \text{Equation VII}$$

wherein $NS_i(x)$ represents a normality score at the $x^{th}$ cycle number of the $i^{th}$ dataset; $D''_i(x)$ represents a second-order change value at the $x^{th}$ cycle number of the $i^{th}$ dataset; $D''_i(x+1)$ represents a second-order change value at the $(x+1)^{th}$ cycle number of the $i^{th}$ dataset; and i and x are each integer of 1 or more.

$$NS_i(x)=D''_i(x)*D''_i(x-1) \qquad \text{Equation VIII}$$

wherein $NS_i(x)$ represents a normality score at the $x^{th}$ cycle number of the $i^{th}$ dataset; $D''_i(x)$ represents a second-order change value at the $x^{th}$ cycle number of the $i^{th}$ dataset; $D''_i(x-1)$ represents a second-order change value at the $(x-1)^{th}$ cycle number of the $i^{th}$ dataset; i is an integer of 1 or more; and x is an integer of 2 or more.

In the Equations VII and VIII, $D''_i(x-1)$, $D''_i(x)$ and $D''_i(x+1)$ indicate second-order difference at cycle number x−1, x and x+1, respectively.

For example, if $D''_1(1)$, $D''_1(2)$, $D''_1(3)$ and $D''_1(4)$ is −100, 50, 350, −400, respectively, $NS_1(1)$, $NS_1(2)$ and $NS_1(3)$ will be −5000 (=−100*50), 17500 (=50*350) and −14000 (=350*−400), respectively, for the Equation VII; while $NS_1(2)$, $NS_1(3)$ and $NS_1(4)$ will be −5000 (=−100*50), 17500 (=50*350) and −14000 (=350*−400), respectively, for the Equation VIII.

It is noted that the normality score at the end cycle number cannot be calculated upon using the Equation VII; whereas the normality score at the first cycle number cannot be calculated upon using the Equation VIII.

It is further noted that the normality scores obtained by the Equation VII and the normality scores obtained by the Equation VIII have certain intercovertibility with respect to cycle numbers.

Specifically, the $NS_i(x)$ obtained by the Equation VII is the same as the normality score at the $NS_i(x+1)$ obtained by the Equation VIII. For example, the normality score at the $4^{th}$ cycle number obtained by the Equation VII is the same as the normality score at the $5^{th}$ cycle number obtained by the Equation VIII. Therefore, in view of such intercovertibility, one of skill in the art can readily convert the normality scores obtained by the Equations VII into the normality scores obtained by the Equation VIII, or vice versa.

The calculation of normality scores by the Equation VII is exemplified in Examples of the present application. However, those skilled in the art will be able to calculate the normality score at each cycle number using the Equation VIII instead of the Equation VII and then adjust the cycle number, i.e., subtract 1 from the calculated cycle number, thereby obtaining the same result as that by the Equation VII.

Meanwhile, the calculation of the normality score using the Equation VII or Equation VIII may be combined with the calculation of the second-order change value using the forward or backward difference method mentioned in step (b) in various ways.

For example, the calculation of the second-order difference using the forward difference method may be combined with the calculation of the normality score using Equation VII; the calculation of the second-order difference using the forward difference method may be combined with the calculation of the normality score using Equation VIII; the calculation of the second-order difference using the backward difference method may be combined with the calculation of the normality score using Equation VII; or the calculation of the second-order difference using the backward difference method may be combined with the calculation of the normality score using Equation VIII.

However, it should be noted that, in such various combinations of either the forward difference method or backward difference method and either the Equation VII or Equation VIII, the cycle number having the same normality score will vary with certain regularity, and thus the cycle number indicative of an abnormal signal will also vary with certain regularity.

For example, where a combination of the forward difference method and the Equation VII yields a normality score of −63 at the $2^{nd}$ cycle number, a combination of the forward difference method and the Equation VIII will yield the same normality score at the $3^{rd}$ cycle number, a combination of the backward difference method and the Equation VII will yield the same normality score at the $4^{th}$ cycle number; and a combination of the backward difference method and the Equation VIII will yield the same normality score at the $5^{th}$ cycle number. Thus, the cycle number indicative of an abnormal signal may vary depending upon the calculation methods of the normality score.

According to an embodiment, the calculation of the normality scores is performed in the same manner for all datasets, e.g., all datasets are subjected to identical calculation methods of second-order change values and normality scores.

The present inventors have verified that a cycle number theoretically determined to be indicative of an abnormal signal by a combination of the backward difference method and the Equation VII exhibits an abnormal signal in a visual inspection on an actual dataset. This proves that the method of present invention using a combination of the backward difference method and the Equation VII is very accurate and effective in determining a cycle number indicative of an abnormal signal. However, considering the above-described rules of cycle number change, one skilled in the art will be able to use other combinations. For example, where a combination of the forward difference method and the Equation VII is used, the cycle number indicative of an abnormal signal may be adjusted by adding cycle number 2 to the result. Therefore, it will be appreciated by one of skill in the art that such various combinations are within the scope of the present invention.

The calculation of the normality score by the combination of the backward difference method and the Equation VII can be also found in Examples of the present application.

Step (d): Determining a Cycle Number Indicative of an Abnormal Signal 140

Finally, the normality scores calculated for each dataset in the step (c) are used to determine a cycle number indicative of an abnormal signal.

As described above, the normality score at a cycle number is highly associated with normality/abnormality of signal value at the cycle number, which may be useful in determining a cycle number(s) indicative of an abnormal signal in a certain dataset. In particular, according to the present method, two or more datasets are obtained in the step (a), each cycle number will have two or more normality scores and such normality scores can be used to determine the normality/abnormality at each cycle number.

In an embodiment, the calculated normality scores per se may be directly used to determine a cycle number indicative of an abnormal signal without any additional processing. For example, a cycle number having a minimum normality score among the calculated normality scores having a negative sign may be determined as a cycle number indicative of an abnormal signal.

In another embodiment, the calculated normality scores may be further processed and then used to determine a cycle number indicative of an abnormal signal.

The two embodiments are referred herein as to "individual normality score approach (direct approach)" and "integrated normality score approach (indirect approach)", respectively.

Figure 2:
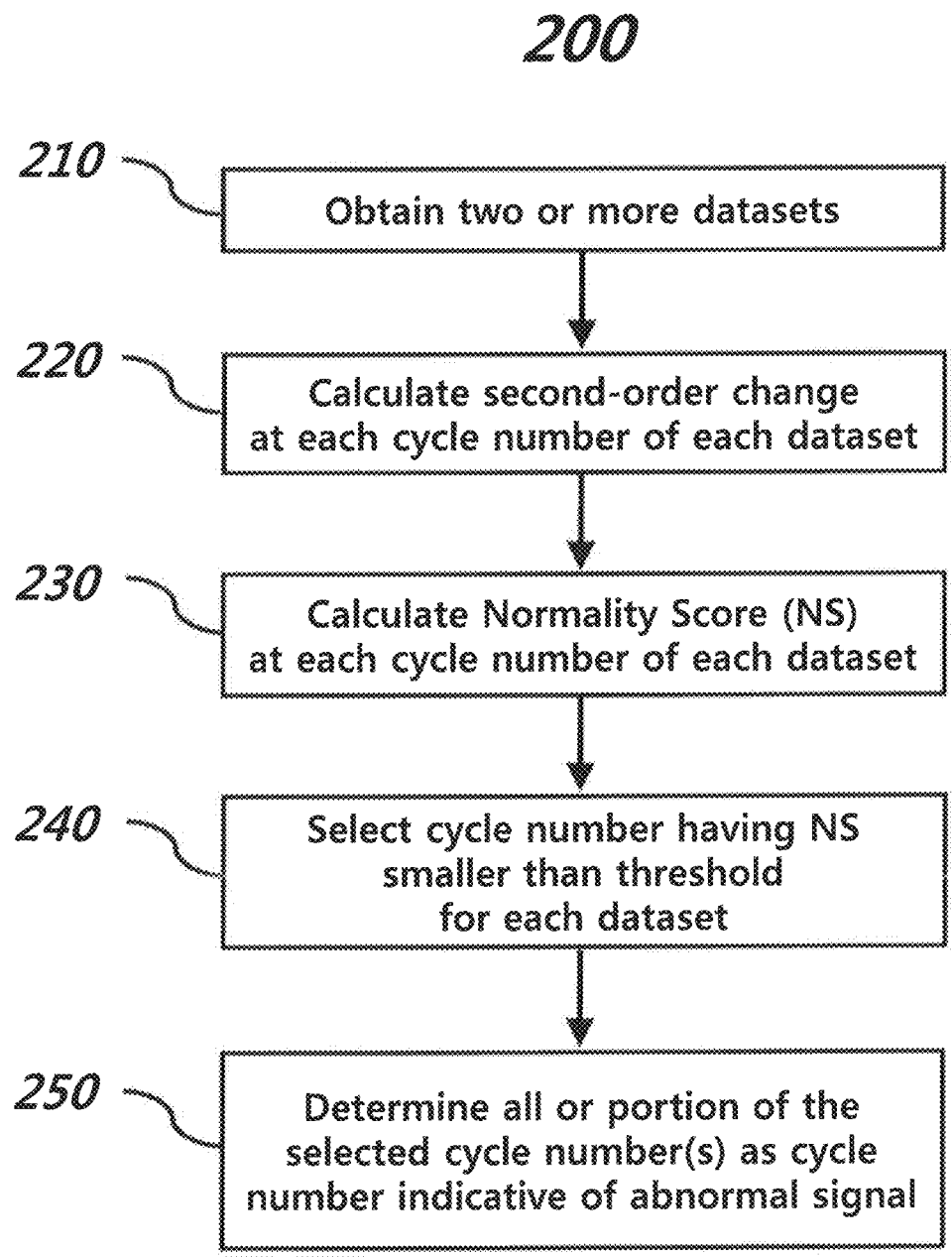
FIG. 2 is a flow chart representing a process for determining a cycle number indicative of an abnormal signal using two or more datasets in accordance with the individual normality score approach.

The two embodiments will be described in detail as below:

(i) Individual Normality Score Approach (FIG. 2; 200)

According to an individual normality score approach, a cycle number(s) indicative of an abnormal signal for each dataset may be determined based on the normality scores as it is.

The individual normality score approach 200 is illustrated in FIG. 2 (In this figure, 210, 220 and 230 correspond to 110, 120 and 130 in FIG. 1, respectively). When referring to FIG. 2, the step (d) is performed by selecting a cycle number(s) as a candidate(s) indicative of an abnormal signal for each dataset, based on normality scores calculated at each cycle number 240, and determining all or a portion of the selected cycle number(s) in all datasets as a cycle number indicative of an abnormal signal for all datasets 250.

The individual normality score approach can be subdivided into "union mode" and "intersection mode", depending upon whether all of the selected cycle number(s) is determined as a cycle number indicative of an abnormal signal for each datasets or a portion of the selected cycle number(s) is determined as a cycle number indicative of an abnormal signal for each dataset.

Hereinafter, the "union mode" and the "intersection mode" will be described in detail.

(i-1) Union Mode

The determination of the cycle number indicative of the abnormal signal in the step (d) may be performed by the so-called "union mode".

According to the union mode, a cycle number(s) satisfying a particular criterion is selected for each dataset, and all of the selected cycle numbers are determined as a cycle number indicative of an abnormal signal for each datasets.

The selection of the cycle number satisfying a particular criterion may be accomplished with or without using a threshold.

The cycle number selected for each dataset may be (i) a cycle number having a normality score smaller than a threshold (e.g., threshold of less than 0); (ii) a cycle number having a normality score which is smaller than a threshold and which is a minimum; or (iii) a cycle number having a negative sign and minimum normality score.

In a first embodiment of the present invention using a threshold, the step (d) is performed by comparing the normality score to a threshold, wherein the threshold is selected from values less than 0; selecting a cycle number having a normality score smaller than the threshold for each dataset; and determining all of the selected cycle numbers for all datasets as a cycle number indicative of an abnormal signal for each datasets.

In the first embodiment, if the $3^{rd}$ cycle number and the $20^{th}$ cycle number are selected for first dataset and the $5^{th}$ cycle number and the $35^{th}$ cycle number are selected for the second dataset as cycle numbers having the normality score smaller than the threshold, the $3^{rd}$, $5^{th}$, $20^{th}$, and $35^{th}$ cycle numbers may be finally determined as the cycle numbers indicative of abnormal signals for all datasets. Alternatively, if the 3$^{rd}$ cycle number and the 20$^{th}$ cycle number are selected for the first dataset and the 3$^{rd}$ cycle number and 4$^{th}$ cycle number are selected for the second dataset, the 3$^{rd}$, 20$^{th}$ and 40$^{th}$ cycle numbers may be finally determined as a cycle number indicative of an abnormal signal for all datasets. It is noted that, for a certain dataset, there may not be a cycle number having a normality score smaller than the threshold.

In a second embodiment of the present invention using a threshold, the step (d) is performed by comparing the normality score to a threshold, wherein the threshold is selected from values less than 0; selecting a cycle number having a normality score which is smaller than the threshold and is the minimum for each dataset, and determining all of the selected cycle numbers as a cycle number indicative of an abnormal signal for each dataset.

In the second embodiment, if the 5$^{th}$ cycle number is selected for the first dataset and the 20$^{th}$ cycle number is selected for the second dataset, the 5$^{th}$ and 20$^{th}$ cycle numbers may be finally determined as a cycle number indicative of an abnormal signal for all datasets. Alternatively, if the 5$^{th}$ cycle number is selected for the first dataset and no cycle number is selected for the second dataset, the 5$^{th}$ cycle number can be finally determined as a cycle number indicative of an abnormal signal for all datasets. It is noted that, for a certain dataset, there may not be a cycle number having a normality score which is smaller than the threshold and which is the minimum.

As described above, a substantial small normality score is associated with a high likelihood of abnormal signal. Thus, for the purpose of selecting a cycle number(s) that is likely to exhibit an abnormal signal, i.e., a cycle number(s) with a substantial small normality score, a threshold may be used in this step.

The threshold to be applied to the normality scores may be selected from values less than 0. The threshold may be determined empirically or experimentally. The threshold may be determined automatically by a device or directly by an operator. The threshold may be a RFU (relative fluorescence unit) of −100, −200, −300, −400, −500, −600, −700, −800, −900, −1000, −2000, −3000, and −4000, including every value in between these numbers.

In a third embodiment of the present invention without using a threshold, the step (d) is performed by selecting a cycle number having a negative sign and minimum normality score for each dataset, and determining all of the selected cycle numbers as a cycle number indicative of an abnormal signal for each datasets.

In the third embodiment, if the 8$^{th}$ cycle number is selected for the first dataset as a cycle number having a minimum normality score and the 15$^{th}$ cycle number is selected for the second dataset as a cycle number having a minimum normality score, the 8$^{th}$ and 15$^{th}$ cycle numbers can be finally determined as a cycle number indicative of an abnormal signal for each datasets.

In any of the three embodiments, no cycle number may be selected for a specific dataset if there is no cycle number satisfying a defined criterion. For example, if there is no cycle number having the normality score of smaller than a threshold in the first dataset, no cycle number is selected for the first dataset.

Where an abnormal signal is detected in any dataset in accordance with one of the embodiments above, a cycle number(s) indicative of an abnormal signal may be corrected or neglected. Alternatively, a dataset including such an abnormal cycle number, or all datasets may be invalidated for re-experimentation.

(i-2) Intersection Mode

The determination of the cycle number indicative of the abnormal signal in the step (d) may be performed by the so-called "intersection mode".

According to the intersection mode, a cycle number(s) satisfying a particular criterion is selected for each dataset, and a portion of the selected cycle numbers are determined as a cycle number indicative of an abnormal signal for each datasets.

The cycle number selected for each dataset may be (i) a cycle number having a normality score smaller than a threshold (e.g., threshold of less than 0); (ii) a cycle number having a normality score which is smaller than a threshold and which is a minimum; or (iii) a cycle number having a negative sign and minimum normality score.

In a first embodiment of the present invention using a threshold, the step (d) is performed by comparing the normality score to a threshold, wherein the threshold is selected from values less than 0; selecting a cycle number having a normality score smaller than the threshold for each dataset; and determining a portion of the selected cycle numbers for all datasets as a cycle number indicative of an abnormal signal for each datasets.

In a second embodiment of the present invention using a threshold, the step (d) is performed by comparing the normality score to a threshold, wherein the threshold is selected from values less than 0; selecting a cycle number having a normality score which is smaller than the threshold and is the minimum for each dataset, and determining a portion of the selected cycle numbers as a cycle number indicative of an abnormal signal for each dataset.

In a third embodiment of the present invention without using a threshold, the step (d) is performed by selecting a cycle number having a negative sign and minimum normality score for each dataset, and determining a portion of the selected cycle numbers as a cycle number indicative of an abnormal signal for each datasets.

In all embodiments as describe above, the portion of the selected cycle numbers to be determined as a cycle number indicative of an abnormal signal for each datasets may be a cycle number(s) commonly selected in 50% or more of all datasets.

In the intersection mode, the degree of commonality of the cycle number may vary depending upon many factors such as the number of datasets, the stringency of the selection of abnormal signals and the like. The commonality of the cycle number may be, for example, more than 50%, more than 60%, more than 70%, more than 80%, more than 90%, or 100% based on the total number of datasets.

According to any of the embodiments above, the step (d) is performed by selecting a cycle number having a normality score smaller than a threshold, a cycle number having a normality score which is smaller than a threshold and which is the minimum, or a cycle number having a negative sign and minimum normality score for each dataset, identifying the commonality of the selected cycle numbers in all datasets, and finally determining a cycle number(s) commonly selected in 50% or more of all datasets as a cycle number indicative of an abnormal signal.

For example, when the 25$^{th}$ cycle number is selected for the first dataset and the 25$^{th}$ cycle number is also selected for the second dataset, the 25$^{th}$ cycle number is finally determined as a cycle number indicating an abnormal signal. In contrast, when the 25$^{th}$ cycle number is selected for the first dataset and the 42$^{nd}$ cycle number is selected for the second dataset, there is no cycle number determined as a cycle number indicative of the abnormal signal.

The meaning of "cycle number(s) commonly selected in 50% or more of all datasets" as used herein will become apparent from the following explanation.

For example, for two datasets obtained by a signal amplification reaction in a single reaction vessel, the cycle number(s) is one which is commonly selected in both datasets (100%). For three datasets obtained by a signal amplification reaction in a single reaction vessel, the cycle number(s) is one which is commonly selected in two datasets (66.7%) or commonly selected in three datasets (100%). For four datasets obtained by a signal amplification reaction in a single reaction vessel, the cycle number(s) is one which is commonly selected in three datasets (75%) or commonly selected in four datasets (100%).

In the intersection mode, an error tolerance (allowable error) may be used when determining a cycle number(s) commonly selected.

The term "error tolerance" refers to an allowable range of cycle numbers to be regarded as common to each other, even if two cycle numbers do not exactly match among datasets.

The present inventors have found that for two datasets obtained by detection at different temperatures, the cycle numbers indicative of an abnormal signal in the two datasets may show a slight variation of 1 or 2 cycle numbers. For example, if performed by the MuDT1 technique developed by the present inventor (WO 2015/147412), a dataset obtained by detection at a relatively low detection temperature (e.g., 60° C.) may exhibit an abnormal signal at a cycle number 10; whereas another dataset obtained by detection at a relatively high detection temperature (e.g., 72° C.) may exhibit an abnormal signal at a cycle number 9 or 8.

In view of such variation in cycle number, an error tolerance with regard to the cycle number is used. When using an error tolerance, two cycle numbers selected for two datasets (e.g., obtained by the detection at the different detection temperatures) may be regarded as being common between the two datasets, as long as these are within an error tolerance. The error tolerance may be within ±2 cycle numbers or within ±1 cycle number. For example, when the 10$^{th}$ cycle number (e.g., having the minimum normality score) is selected for a dataset obtained by detection at the relatively low detection temperature and the 9$^{th}$ cycle number is selected (e.g., having the minimum normality score) for another dataset obtained by detection at the relatively high detection temperature, either the 10$^{th}$ cycle number or the 9$^{th}$ cycle number may be regarded as being commonly selected in two datasets.

Where a cycle number indicative of an abnormal signal is determined by the intersection mode, only the dataset containing the abnormal signal may be corrected, or the dataset containing the abnormal signal as well as the dataset containing no abnormal signal may be corrected. Alternatively, only the dataset containing the abnormal signal, or all datasets used may be invalidated or retested. The correction, invalidation or retest of the datasets may be performed by a number of methods known in the art.

Figure 3:
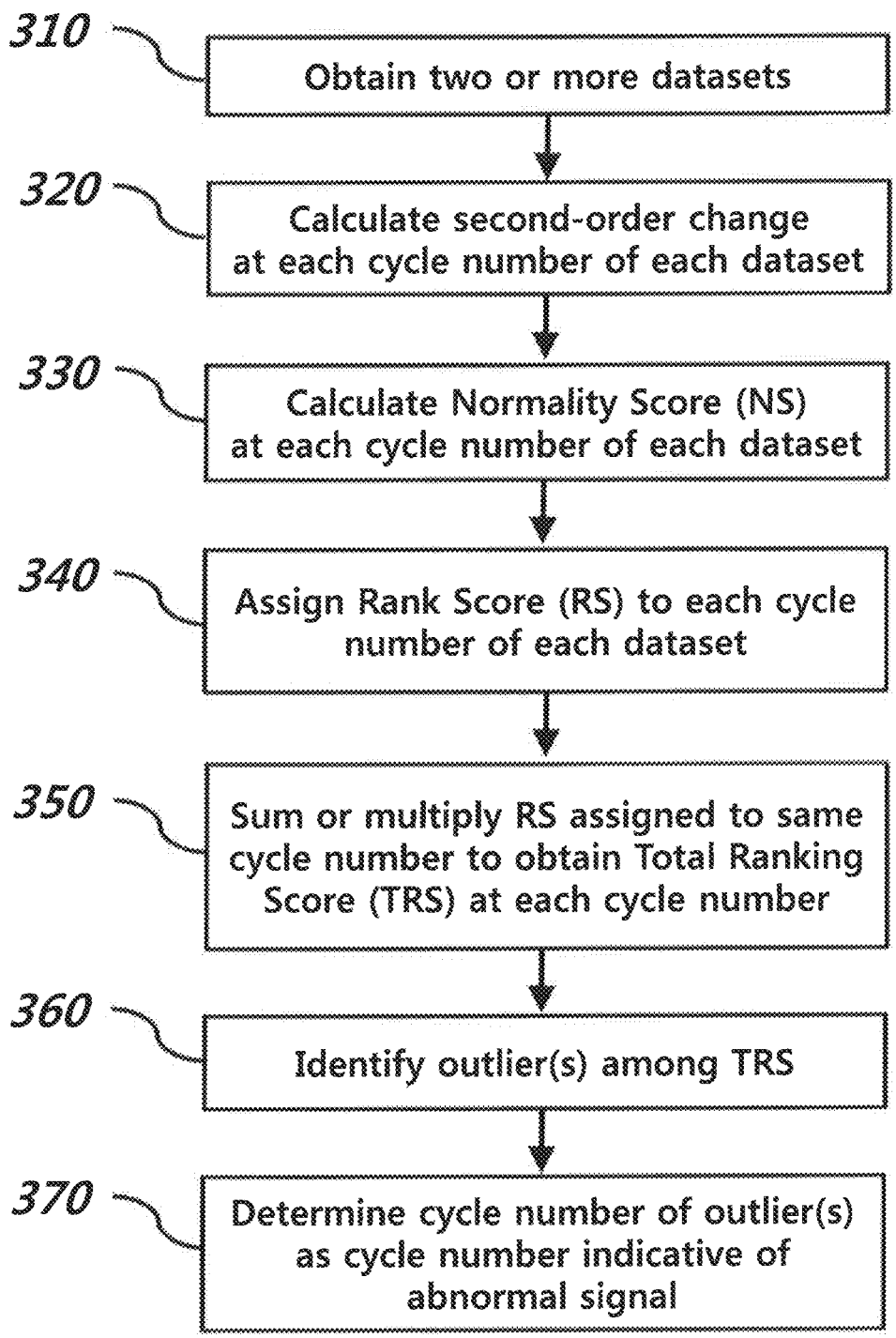
FIG. 3 is a flow chart representing a process for determining a cycle number indicative of an abnormal signal using two or more datasets in accordance with the integrated normality score approach.

(ii) Integrated Normality Score Approach (FIG. 3; 300)

The determination of the cycle number indicative of the abnormal signal in the step (d) may be performed by using a total ranking score (TRS), a new parameter derived from a normality score as described above.

The integrated normality score approach is also referred to as "outlier detection approach".

The integrated normality score approach 300 is illustrated in FIG. 3 (In this figure, 310, 320 and 330 correspond to 110, 120 and 130 in FIG. 1, respectively).

When referring to FIG. 3, the step (d) is performed as follows:

(d-1) assigning a ranking score to each cycle number of each dataset according to the magnitude of its normality score 340;

(d-2) summing or multiplying the ranking scores assigned to the same cycle number of each dataset, to obtain a total ranking score at each cycle number 350;

(d-3) identifying an outlier(s) among the total ranking scores 360; and (d-4) determining a cycle number(s) of the outlier(s) as a cycle number indicative of an abnormal signal 370.

The sub-steps of the integrated normality score approach are described in detail below:

(d-1) Assignment of Ranking Score (RS) 340

In this sub-step, a ranking score (RS) is assigned to each cycle number of each dataset according to the magnitude of its normality score 340.

In the sub-step (d-1), the ranking score may be assigned to each cycle number of each dataset in a number of ways.

In a first embodiment for assigning a ranking score, the sub-step (d-1) is performed by assigning a smaller ranking score to a cycle number having a smaller normality score.

According to the first embodiment, all normality scores calculated at all cycle numbers in the step (c) are arranged in ascending order, and a relatively small ranking score may be assigned to a cycle number having a relatively small normality score and a relatively large ranking score may be assigned to a cycle number having a relatively large normality score. Specifically, in the case that a dataset consists of a total of 45 cycle numbers and ranking scores are assigned at intervals of "1", starting from "1", the smallest ranking score "1" may be assigned to a cycle number having the smallest normality score, and other ranking scores, e.g., 2, 3, 4, 5 . . . , may be sequentially assigned to other cycle numbers based on their magnitude. For instance, when normality scores, −500, 200, 2000 and −3500, are calculated at cycle numbers 1, 2, 3 and 4, respectively, the normality scores may be arranged in ascending order, e.g., in an order of −3500 (4$^{th}$ cycle number), −500 (1$^{st}$ cycle number), 200 (2$^{nd}$ cycle number) and 2000 (3$^{rd}$ cycle number), and then the cycle numbers 4, 1, 2 and 3 will be given ranking scores 1, 2, 3 and 4 based on their magnitude, respectively. It is noted that, when the normality score is calculated by using Equation VII, particularly for a dataset consisting of a total of 45 cycle numbers, ranking scores from 1 to 43 only may be assigned (i.e., ranking scores 44 and 45 does not exist); whereas when the normality score may be calculated by using Equation VIII, ranking scores from 1 to 42 only are assigned (i.e., ranking scores 43, 44 and 45 does not exist).

In a second embodiment for assigning a ranking score, the sub-step (d-1) is performed by assigning a larger ranking score to a cycle number having a smaller normality score.

According to the second embodiment, all normality scores calculated at all cycle numbers in the step (c) may be arranged in descending order according to their magnitude, and a relatively large ranking score may be assigned to a cycle number having a relatively small normality score and a relatively small ranking score may be assigned to a cycle number having a relatively large normality score. Specifically, in the case that a dataset consists of a total of 45 cycle numbers and ranking scores are assigned at intervals of "1", starting from "1", the smallest ranking score "1" may be assigned to a cycle number having the largest normality score, and other ranking scores, e.g., 2, 3, 4, 5 . . . , may be sequentially assigned to other cycle numbers based on their magnitude. For instance, when normality scores, −500, 200, 2000 and −3500, are calculated at cycle numbers 1, 2, 3 and 4, respectively, the normality scores may be arranged in descending order, e.g., in an order of 2000 ($3^{rd}$ cycle number), 200 ($2^{nd}$ cycle number), −500 ($1^{st}$ cycle number) and −3500 ($4^{th}$ cycle number), and then the cycle numbers 3, 2, 1 and 4 will be given ranking scores 1, 2, 3 and 4 based on their magnitude, respectively. It is noted that, when the normality score is calculated by using Equation VII, particularly for a dataset consisting of a total of 45 cycle numbers, ranking scores from 1 to 43 only may be assigned (i.e., ranking scores 44 and 45 does not exist); whereas when the normality score is calculated by using Equation VIII, ranking scores from 1 to 42 only may be assigned (i.e., ranking scores 43, 44 and 45 does not exist).

According to the integrated normality score approach, the ranking scores may be assigned in a regular manner. Specifically, the ranking scores may be assigned at regular intervals.

For example, a ranking score of "1" is first assigned to a cycle number having the smallest normality score (minimum normality score), and then ranking scores (e.g., 2, 3, 4, . . . ) with common difference are successively assigned to other cycle numbers based on their normality scores. The common difference may be various values. Also, a ranking score of "300" is first assigned to a cycle number having the smallest normality score, and then ranking scores with common difference (e.g., 500, 700, 900, . . . ) are successively assigned to other cycle numbers. The scoring system may vary depending upon the user.

(d-2) Obtaining Total Ranking Score (TRS) 350

In this sub-step, a total ranking score (TRS) is obtained by summing or multiplying the ranking scores assigned to the same cycle number of each dataset 350.

The total ranking score (TRS) at each cycle number may be calculated by a mathematical operation including addition or multiplication of ranking scores assigned to the same cycle number for each dataset in the sub-step (d-2). The mathematical operations may be accomplished by any equation involving the addition or multiplication of ranking scores.

According to an embodiment of the present invention, the total ranking score in the sub-step (d-2) is obtained by summing ranking scores assigned to the same cycle number of each dataset.

Specifically, when four datasets are obtained in the step (a), a total ranking score of the $1^{st}$ cycle number may be obtained by summing all four ranking scores at the $1^{st}$ cycle number of the four datasets. For example, where a $1^{st}$ dataset has ranking scores of 19, 27, 3, and 10 at cycle numbers of 1, 2, 3 and 4 and where a $2^{nd}$ dataset has ranking scores of 40, 16, 1 and 30 at cycle numbers of 1, 2, 3 and 4 and where a $3^{rd}$ dataset has ranking scores of 21, 10, 2 and 8 at cycle numbers of 1, 2, 3 and 4, total ranking scores at cycle numbers of 1, 2, 3 and 4 will be 80 (=19+40+21), 53 (=7+16+10), 6 (=3+1+2) and 19 (=10+1+8), respectively.

The "ranking score" provides fragmentary information about normality/abnormality of each cycle number with regard to one dataset, while the "total ranking score" provides comprehensive information about normality/abnormality of each cycle number with regard to entire datasets. Therefore, the latter may be more useful in analyzing abnormal signals.

(d-3) Identification of Outlier(s) 360

In this sub-step, an outlier(s) is identified among the total ranking scores 360.

The term "outlier" as used herein refers to a total ranking score that is numerically distant from (deviates so much from) the rest of the total ranking scores. The term "outlier" also refers to a total ranking score that is sufficiently dissimilar from all the other total ranking scores in the set of total ranking scores.

The outlier may be identified by a number of outlier detection methods known in the art.

Exemplary outlier detection methods are as follows.

Outlier detection methods can be divided between univariate methods, proposed in earlier works in this field, and multivariate methods that usually form most of the current body of research. Another fundamental taxonomy of outlier detection methods is between parametric (statistical) methods and nonparametric methods that are model-free (e.g., see Williams et al., "A Comparative Study of RNN for Outlier Detection in Data Mining," IEEE International Conference on Data-mining (ICDM'02), Maebashi City, Japan, CSIRO Technical Report CMIS-02/102, 2002).

Other example of the outlier detection methods includes standard deviation (SD) method, Z-score, modified Z-score, Tukey's method (boxplot), adjusted boxplot, $MAD_e$ (median and Median Absolute Deviation) method, and median rule.

According to an embodiment, the outlier(s) may be identified by the univariate method and the nonparametric method. The present inventors have contemplated the "gap mode" or "threshold mode" which is a certain embodiment of the univariate method and the nonparametric method. The two modes will be explained in detail as below.

Gap Mode

The gap mode is an approach of arranging the total ranking scores, identifying an 'outlier gap', and then finding a cycle number indicative of an abnormal signal via the outlier gap.

In an embodiment of the gap mode, the sub-step (d-3) is performed by (i) arranging the total ranking scores at each cycle number in the order of magnitude; (ii) calculating a gap between two neighboring total ranking scores in the arrangement; (iii) identifying an outlier gap in the arrangement; and (iv) determining as an outlier(s) a total ranking score smaller than or equal to a relatively small total ranking score out of two neighboring total ranking scores of the outlier gap, or determining as an outlier(s) a total ranking score larger than or equal to a relatively large total ranking score out of two neighboring total ranking scores of the outlier gap.

First, the total ranking scores at all cycle numbers are arranged in the order of magnitude. The total ranking scores may be arranged in ascending or descending order according to the magnitude. The total ranking scores may be one-dimensionally arranged. An outlier gap is identified by the distance between two neighboring total ranking scores in the arrangement.

Second, a gap between two neighboring total ranking scores is calculated in the arrangement. The term "gap" as used herein refers to a section between two immediately adjacent total ranking scores in an arrangement, or a magnitude thereof. In particular, the gap means an interval or a distance or magnitude thereof between adjacent total ranking scores in the arrangement according to the gap mode of the present invention. The gap consists of two neighboring total ranking scores, i.e., a relatively large total ranking score and a relatively small total ranking score, and the calculation of the gap may be performed by subtracting the relatively small total ranking score from the relatively large total ranking score. For example, when the relatively large total ranking score and the relatively small total ranking score of the two consecutive total ranking scores in an arrangement are 50 and 45, respectively, the calculated gap is 5.

Third, an outlier gap is identified in the arrangement. The term "outlier gap" as used herein refers to a gap that is significantly larger in size than the rest of the gaps. The outlier gap can be identified by various ways.

The outlier gap may be (i) a gap having the largest size; (ii) one of a gap having the largest size and a gap having the second largest size; or (iii) one of gap(s) deviating from the mean gap size.

In a first embodiment for identifying an outlier gap, a gap having the largest size is identified as an outlier gap. For example, in an arrangement consisting of total ranking scores 4, 46, 50, 58 and 72 in ascending order, a section from a total ranking score "4" to a total ranking score "46" (largest gap) may be identified as an outlier.

In a second embodiment for identifying an outlier gap, one of a gap having the largest size and a gap having the second largest size is identified as an outlier gap. For example, in an arrangement consisting of total ranking scores 4, 46, 50, 58 and 72 in ascending order, either a section from a total ranking score "4" to a total ranking score "46" (largest gap: gap size 40) or a section from a total ranking score "58" to a total ranking score "72" (second largest gap: gap size 14) may be identified as an outlier.

In the second embodiment, the largest gap or the second largest gap is identified as an outlier gap, depending upon the scoring system of ranking score in the sub-step (d-1), as follows:

(i) In the case of assigning a smaller ranking score to a cycle number having a smaller normality score in each dataset in the sub-step (d-1), out of the largest gap and the second largest gap, a gap close to the smallest total ranking score in an arrangement may be identified as an outlier. For example, in an arrangement consisting of total ranking scores 4, 46, 50, 58 and 72, a section from a total ranking score "4" to a total ranking score "46" (largest gap: gap size 42) may be identified as an outlier, because the largest gap is close to the smallest total ranking score "4" compared to the second largest gap. As another example, in an arrangement consisting of total ranking scores 4, 18, 23, 33 and 53, a section from a total ranking score "4" to a total ranking score "18" (second largest gap: gap size 14) may be identified as an outlier, because the second largest gap is close to the smallest total ranking score "4" compared to the largest gap; and (ii) In the case of assigning a larger ranking score to a cycle number having a smaller normality score in each dataset in the sub-step (d-1), out of the largest gap and the second largest gap, a gap close to the largest total ranking score in an arrangement may be identified as an outlier. For example, in an arrangement consisting of total ranking scores 6, 24, 29, 37 and 72, a section from a total ranking score "37" to a total ranking score "72" (largest gap) may be identified as an outlier, because the largest gap is close to the largest total ranking score "72" compared to the second largest gap. As another example, in an arrangement consisting of total ranking scores 6, 41, 48, 52 and 72, a section from a total ranking score "52" to a total ranking score "72" (second largest gap) may be identified as an outlier, because the second largest gap is close to the largest total ranking score "72" compared to the largest gap.

In a third embodiment, one of gap(s) deviating from the mean gap size is identified as an outlier gap. If there is a single gap deviating from the mean gap size, the single gap may be identified as an outlier gap. However, if there are multiple gaps deviating from the mean gap size, only one gap among the multiple gaps may be identified as an outlier gap, depending upon the scoring system of ranking score in the sub-step (d-1), as follows:

(i) In the case of assigning a smaller ranking score to a cycle number having a smaller normality score in each dataset in the sub-step (d-1), out of multiple gaps deviating from the mean gap size, a gap close to the smallest total ranking score in an arrangement may be identified as an outlier. For example, in an arrangement consisting of total ranking scores 4, 46, 50, 58 and 72, a section from a total ranking score "4" to a total ranking score "46" may be identified as an outlier, because the size of the gap (42) only deviates from the mean gap size (17; =(42+4+8+14)/4). As another example, in an arrangement consisting of total ranking scores 4, 18, 23, 33 and 53 in ascending order, a section from a total ranking score "4" to a total ranking score "18" may be identified as an outlier, because out of multiple gaps (i.e., one section from a total ranking score "4" to a total ranking score "18" and another section from a total ranking score "33" to a total ranking score "53") deviating from the mean gap size (12.25; =(14+5+10+20)/4), the section from a total ranking score "4" to a total ranking score "18" is close to the smallest total ranking score "4"; and (ii) In the case of assigning a larger ranking score to a cycle number having a smaller normality score in each dataset in the sub-step (d-1), out of multiple gaps deviating from the mean gap size, a gap close to the largest total ranking score in an arrangement may be identified as an outlier. For example, in an arrangement consisting of total ranking scores 10, 24, 29, 37 and 72 in ascending order, a section from a total ranking score "37" to a total ranking score "72" may be identified as an outlier, because the size of the gap (35) only deviates from the mean gap size (15.5; =(14+5+8+35)/4). As another example, in an arrangement consisting of total ranking scores 6, 41, 48, 52 and 72, a section from a total ranking score "52" to a total ranking score "72" may be identified as an outlier, because out of multiple gaps (i.e., one section from a total ranking score "6" to a total ranking score "41" and another section from a total ranking score "52" to a total ranking score "72") deviating from the mean gap size (16.5; =(35+7+4+20)/4), the section from a total ranking score "52" to a total ranking score "72" is close to the largest total ranking score "72"

Although only the mean gap size is mentioned in the above embodiments, it will be appreciated by one of skill in the art that various other criteria may be used instead of the mean gap size. For example, one, two, three, four, five, or six standard deviation of the mean may be used instead of the mean gap size. In particular, one of gap(s) deviating from three standard deviation of the mean gap size (mean+3*S.D) may be identified as an outlier gap.

In an embodiment, a gap having a size smaller than a predetermined size may be excluded from an outlier gap. For example, in a method of identifying the largest gap as an outlier gap, when the largest gap is smaller than the predetermined size, the gap may be regarded as not being an outlier gap.

Meanwhile, where there are a plurality of gaps having the same size in the arrangement, the method of selecting one of the two or more candidate gaps may be applied for identification of the outlier.

As another method for identifying an outlier gap, the size of the gap is compared to a relatively small total ranking score of the gap, and if the gap size is larger than the relatively small total ranking score, the gap is identified as the outlier gap. If there are multiple gaps, the size of which is larger than a relatively small total ranking score of the gap, one of them may be identified as an outlier.

As an alternative of aforementioned embodiments, the outlier gap identified by any one of the aforementioned embodiments may be neglected, depending upon the position of the gap. The gap identified within a particular number of total ranking scores in an arrangement may be regarded as a non-outlier gap. Specifically, the gap identified within 7, 8, 9, 10, 11, 12, 13, 14, 15, 16, 17, 18, 19 or 20 total ranking score in an arrangement may be regarded as a non-outlier gap. For example, even if a gap having the largest size is positioned between $13^{th}$ total ranking score to $14^{th}$ total ranking score, the gap may be regarded as a non-outlier gap. The criteria may vary.

In the three embodiments for identifying an outlier gap, a reference total ranking score may be further used.

Even in the case of datasets consisting only of cycle numbers indicative of a normal signal, there is an outlier gap identified in the arrangement, and a cycle number indicative of normal signal may be erroneously determined as a cycle number indicative of an abnormal signal. Therefore, a reference total ranking score can additionally be used in order to avoid such problem. The use of a reference total ranking score results in the formation of a new gap at either terminus in the arrangement and allows the newly formed gap to be identified as an outlier gap, thereby reducing the possibility of misjudging a cycle number indicative of a normal signal as a cycle number indicative of an abnormal signal.

The reference total ranking score is a virtual or imaginary value. In an embodiment, the reference total ranking score is an additional total ranking score that is smaller than all of the total ranking scores in the arrangement. In an embodiment, the reference total ranking score is an additional total ranking score that is larger than all of the total ranking scores in the arrangement.

According to an embodiment, the reference total ranking score is smaller or larger than all of the total ranking scores in the arrangement, depending upon the scoring system of ranking score in the sub-step (d-1).

According to an embodiment, the reference total ranking score is selected such that the gap to be newly formed at either terminus of the arrangement by the use of the reference total ranking score is the largest among all gaps in datasets consisting only of cycle numbers indicative of a normal signal.

According to an embodiment, the reference total ranking score is selected to obtain a desired gap size at either terminus of the arrangement. The desired gap size may be adjusted. For example, in an embodiment of identifying a maximum gap as an outlier(s), the desired gap size may be adjusted to be the largest among all gaps or smaller than a maximum gap.

The reference total ranking score does not have a corresponding cycle number. Accordingly, even if the reference total ranking score is determined as an outlier, there is no cycle number to be determined as being indicative of an abnormal signal. The use of the reference total ranking score is not intended to further add a cycle number indicative of an abnormal signal.

The reference total ranking score may be obtained by (i) further assigning a reference ranking score to each dataset, wherein the reference ranking score is smaller than all ranking scores assigned to all cycle numbers in the sub-step (d-1) when a smaller ranking score is assigned to a cycle number having a smaller normality score in each dataset in the sub-step (d-1) or the reference ranking score is larger than all ranking scores assigned to all cycle numbers in the sub-step (d-1) when a larger ranking score is assigned to a cycle number having a smaller normality score in each dataset in the sub-step (d-1); and (ii) summing the reference ranking scores assigned to all datasets.

In the case of assigning a smaller ranking score to a cycle number having a smaller normality score in each dataset in the sub-step (d-1), a reference ranking score to be assigned may be smaller than all ranking scores assigned to all cycle numbers. In particular, the reference ranking score may be assigned at regular intervals, considering all ranking scores assigned to all cycle numbers. For example, when ranking scores are assigned to all cycle numbers in regular intervals of score 1, e.g., 1, 2, 3 . . . , a reference ranking score may be "0".

In the case of assigning a larger ranking score to a cycle number having a smaller normality score in each dataset in the sub-step (d-1), a reference ranking score to be assigned may be larger than all ranking scores assigned to all cycle numbers. In particular, the reference ranking score may be assigned at regular intervals, considering all ranking scores assigned to all cycle numbers. For example, when ranking scores are assigned to all cycle numbers in regular intervals of score 1, e.g., 1, 2, 3 . . . , 41, 42 and 43, a reference ranking score may be "44".

The reference ranking scores assigned to all datasets are summed to obtain a reference total ranking score.

In the case of assigning a smaller ranking score to a cycle number having a smaller normality score in each dataset in the sub-step (d-1) and a reference ranking score of "0" is assigned to each of three datasets, a reference total ranking score may be "0" (0+0+0).

In the case of assigning a larger ranking score to a cycle number having a smaller normality score in each dataset in the sub-step (d-1) and a reference ranking score of "44" is assigned to each of three datasets, a reference total ranking score may be "132" (44+44+44).

The reference total ranking score may be inserted or introduced into the arrangement of the total ranking scores, and the set of the total ranking scores including the reference total ranking score is used to identify an outlier gap.

Fourth, a total ranking score smaller than or equal to a relatively small total ranking score out of two neighboring total ranking scores of the outlier gap is determined as an outlier(s), or a total ranking score larger than or equal to a relatively large total ranking score out of two neighboring total ranking scores of the outlier gap is determined as an outlier(s).

The total ranking score to be determined as an outlier may vary depending upon the scoring system of ranking score in the sub-step (d-1), as follows:

In case of assigning a smaller ranking score to a cycle number having a smaller normality score in each dataset in the sub-step (d-1), a total ranking score smaller than or equal to a relatively small total ranking score out of two neighboring total ranking scores of the outlier gap is determined as an outlier(s). For example, assuming that there is four total ranking scores "a", "b", "c" and "d" (wherein, a<b<c<d) arranged in ascending order and the outlier gap is a section between "c" and "d", the total ranking scores "a", "b", and "c", which are smaller than or equal to a relatively small total ranking score "c" of the outlier gap are determined as an outlier(s).

In case of assigning a larger ranking score to a cycle number having a smaller normality score in each dataset in the sub-step (d-1), a total ranking score larger than or equal to a relatively large total ranking score out of two neighboring total ranking scores of the outlier gap is determined as an outlier(s). For example, assuming that there is four total ranking scores "a", "b", "c" and "d" (wherein, a<b<c<d) arranged in ascending order and the outlier gap is a section between "c" and "d", the total ranking score "d", which is larger than or equal to a relatively large total ranking score "d" of the outlier gap are determined as an outlier(s).

Alternatively, the outlier(s) may be identified by "threshold mode".

Threshold Mode

The step (d-3) for identifying an outlier(s) may be performed with a defined threshold.

According to the threshold mode, the sub-step (d-3) may be performed by applying a threshold to the total ranking scores and determining as an outlier(s) a total ranking score smaller than the threshold or determining as an outlier(s) a total ranking score larger than the threshold.

The identification of outlier may vary depending upon the scoring system of ranking score in the sub-step (d-1), as follows:

(i) In the case of assigning a smaller ranking score to a cycle number having a smaller normality score in each dataset in the sub-step (d-1), the sub-step (d-3) is performed by determining as an outlier(s) a total ranking score smaller than the threshold; and (ii) In the case of assigning a lager ranking score to a cycle number having a smaller normality score in each dataset in the sub-step (d-1), the sub-step (d-3) is performed by determining as an outlier(s) a cycle number having a total ranking score larger than the threshold.

The threshold to be applied to the total ranking scores may be suitably selected. The threshold may be determined automatically by the detector or directly by the operator.

According an embodiment, a combination of the gap mode and the threshold mode may be used to identify an outlier(s).

(d-4) Determination of a Cycle Number Indicative of an Abnormal Signal

In this sub-step, a cycle number(s) of the outlier identified in the step (d-3) is determined as a cycle number indicative of an abnormal signal.

Since all total ranking scores except for a reference total ranking score have corresponding cycle numbers, the outlier identified in the sub-step (d-3) can be readily switched to a cycle number indicative of an abnormal signal.

For example, assuming that there are four total ranking scores, 5, 30, 36 and 41 (corresponding to the cycle numbers 3, 15, 40 and 33 respectively) and the total ranking score "5" is identified as an outlier in the sub-step (d-3), a cycle number "3" corresponding to the total ranking score "5" can be determined as a cycle number indicative of an abnormal signal.

Meanwhile, the determination of a cycle number indicative of an abnormal signal in the step (d) is performed by any combination of the aforementioned methods.

In an embodiment, the determination of a cycle number indicative of an abnormal signal in the step (d) may be performed by a combination of any union mode, any intersection mode, any gap mode, and any threshold mode.

For example, the determination of a cycle number indicative of an abnormal signal in the step (d) may be performed by a combination of any intersection mode and any gap mode (see Example 3), or a combination of any intersection mode, any gap mode, and any threshold mode. These combinations may allow more accurate determination of abnormal signals.

As a result of such combination, a common cycle number(s) may be finally determined as a cycle number indicative of an abnormal signal.

According to another aspect of the present invention, there is provided a method for detecting an abnormal signal using two or more datasets, comprising:

(a) obtaining two or more datasets by a signal amplification reaction in a single reaction vessel; wherein each of the datasets comprises a plurality of data points; wherein each of the data points has a cycle number and a signal value at the cycle number; and (b) determining a cycle number indicative of an abnormal signal for each dataset, based on a commonly sharing feature between abnormal signals in the two or more datasets; wherein the commonly sharing feature is (i) a reaction environmental feature surrounding the generation of the abnormal signals or (i) a signal-specifying feature of the abnormal signals.

According to the method, a cycle number indicative of an abnormal signal can be determined by a reaction environmental feature surrounding the generation of the abnormal signals. The reaction environmental feature surrounding the generation of the abnormal signals indicates the same reaction environment such as a single reaction vessel, which may affect all datasets and be used to identify abnormal signals. Further, according to the method, a cycle number indicative of an abnormal signal can be determined by a signal-specifying feature of the abnormal signals. The signal-specifying feature of the abnormal signals includes features which can be used to identify abnormal signals, such as the commonality of the cycle numbers, the normality scores, the shape of the abnormal signal and the like.

According to a first embodiment, there is provided a method for detecting an abnormal signal using two or more datasets, comprising the steps of:

(a) obtaining two or more datasets by a signal amplification reaction in a single reaction vessel; wherein each of the datasets comprises a plurality of data points; wherein each of the data points has a cycle number and a signal value at the cycle number;

(b) analyzing each dataset individually to select a cycle number indicative of an abnormal signal from each dataset; and (c) determining all or a portion of the selected cycle numbers as a cycle number indicative of an abnormal signal for each dataset.

According to a second embodiment, there is provided a method for detecting an abnormal signal using two or more datasets, comprising the steps of:

(a) obtaining two or more datasets by a signal amplification reaction in a single reaction vessel; wherein each of the datasets comprises a plurality of data points; wherein each of the data points has a cycle number and a signal value at the cycle number; and (b) analyzing all datasets in integrated manner to provide a cycle number(s) indicative of an abnormal signal in all datasets;

(c) determining the provided cycle number(s) as a cycle number indicative of an abnormal signal for each dataset.

According to the second embodiment, there is further provided a method for detecting an abnormal signal using two or more datasets, comprising the steps of:

(a) obtaining two or more datasets by a signal amplification reaction in a single reaction vessel; wherein each of the datasets comprises a plurality of data points; wherein each of the data points has a cycle number and a signal value at the cycle number;

(b) analyzing all datasets in integrated manner to identify a cycle number(s) corresponding to a outlier(s); and (c) determining the cycle number(s) of the outlier(s) as a cycle number indicative of an abnormal signal for each dataset.

An example of the first embodiment is the "intersection mode" or "union mode" as described above, and an example of the second embodiment is the "gap mode" or the "threshold mode".

According to an embodiment of the present invention, the present invention further comprises a step of correcting the signal value at the cycle number indicative of the abnormal signal.

The correction may be performed according to various methods known in the art. As one example, the signal value at the cycle number immediately before or after the cycle number indicative of the abnormal signal may be adopted as the correction value. Alternatively, the average of the signal values at the cycle numbers before and after the cycle number indicative of the abnormal signal may be adopted as the correction value.

According to an embodiment of the present invention, the present invention further comprises a step of invalidating the signal value at the cycle number indicative of the abnormal signal. Alternatively, the present invention may further comprise invalidating the cycle number indicative of the abnormal signal or invalidating the dataset including the cycle number indicative of the abnormal signal.

The correction and the invalidation may be performed automatically by a computer program, or may be performed directly by the practitioner. For example, when performed by a computer program, a cycle number to be corrected or invalidated or a dataset to be invalidated may be displayed on the display. In the case of invalidation, an indication may be displayed on the display indicating the object to be retested.

II. Storage Medium, Computer Program and Device for Signal Extraction

Since the storage medium, the device and the computer program of the prevent invention described hereinbelow are intended to perform the present methods in a computer, the common descriptions between them are omitted in order to avoid undue redundancy leading to the complexity of this specification.

In another aspect of this invention, there is provided computer readable storage medium containing instructions to configure a processor to perform a method for detecting an abnormal signal using two or more datasets, comprising:

(a) receiving two or more datasets by a signal amplification reaction in a single reaction vessel; wherein each of the datasets comprises a plurality of data points; wherein each of the data points has a cycle number and a signal value at the cycle number;

(b) calculating a second-order change value at each cycle number of each dataset;

(c) calculating a normality score at each cycle number of each dataset by using the second-order change value; wherein the calculation of the normality score is performed by a mathematical operation that represents sign change between and magnitudes of the second-order change values at two consecutive cycle numbers; and (d) determining a cycle number indicative of an abnormal signal by using the normality score.

In still another aspect of this invention, there is provided a computer program to be stored on a computer readable storage medium to configure a processor to perform a method for detecting an abnormal signal using two or more datasets, the method comprising:

(a) receiving two or more datasets by a signal amplification reaction in a single reaction vessel; wherein each of the datasets comprises a plurality of data points; wherein each of the data points has a cycle number and a signal value at the cycle number;

(b) calculating a second-order change value at each cycle number of each dataset;

(c) calculating a normality score at each cycle number of each dataset by using the second-order change value; wherein the calculation of the normality score is performed by a mathematical operation that represents sign change between and magnitudes of the second-order change values at two consecutive cycle numbers; and (d) determining a cycle number indicative of an abnormal signal by using the normality score.

The program instructions are operative, when performed by the processor, to cause the processor to perform the present method described above. The program instructions for performing the present method may comprise (i) an instruction to calculate a second-order change value at each cycle for each dataset; (ii) an instruction to calculate a normality score at each cycle number by using the second-order change value; and (iii) an instruction to determine a cycle number indicative of an abnormal signal by using the normality score.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The signal values from the signal-generating process may be received through several mechanisms. For example, the signal values may be acquired by a processor resident in a PCR data acquiring device. The signal values may be provided to the processor in real time as the signal values are being collected, or it may be stored in a memory unit or buffer and provided to the processor after the experiment has been completed. Similarly, the signal values may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the dataset may be provided to a server system via a network connection (e.g., LAN, VPN, intranet, Internet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In a further aspect of this invention, there is provided a device for detecting an abnormal signal using two or more datasets, comprising (a) a computer processor and (b) the computer readable storage medium described above coupled to the computer processor.

According to an embodiment, the device further comprises a reaction vessel to accommodate the sample and signal-generating means, a temperature controlling means to control temperatures of the reaction vessel and/or a detector to detect signals at cycle numbers.

The processor may be prepared in such a manner that a single processor can do several performances. Alternatively, the processor unit may be prepared in such a manner that several processors do the several performances, respectively.

According to an embodiment, the processor may be embodied by installing software into conventional devices for detection of target nucleic acid sequences (e.g. real-time PCR device).

The signal values may be received with amplification curves in various fashions. For example, the signal values may be received and collected by a processor in a data collector of the real-time PCR device. Upon collecting the signal values, they may be provided to a processor in a real-time manner, or stored in a memory unit or buffer and then provided to a processor after experiments.

Likely, the signal values may be provided from the real-time PCR device to the computer system such as a desktop computer system via network connection (e.g., LAN, VPN, intranet and internet) or direct connection (e.g., USB and wired or wireless direct connections), or via portable media such as CD, DVD, floppy disk and portable HDD. Alternatively, the signal values may be provided to a server system via network connections (e.g., LAN, VPN, intranet, internet and wireless communication network) connected to a client such as notebook and desktop computer systems.

As described above, the present method may be embodied by an application (i.e., program) supplier-installed or user-direct installed into the computer system, and recorded in a computer readable storage medium.

A computer program embodying the present method may implement all functions for detection of abnormal signal. The computer program may a program comprising program instructions stored on a computer readable storage medium to configure a processor to perform the present method.

The computer program may be coded by using suitable computer languages such as C, C++, JAVA, Visual basic, VBScript, JavaScript, Perl, XML and machine languages. The program codes may include function codes for mathematical functions described above and control codes for implementing process in order by a processor of the computer system.

The codes may further comprise memory reference codes by which additional information or media required in implementing the above-described functions by the processor is referred at location (address) of internal or external memory of the computer system.

When the computer system requires communication with another computer or server in remote for implementing functions of the processor, the codes may further comprise communication-relating codes encoding how the processor is communicated with another computer or server in remote by using communication module (e.g., wired and/or wireless communication module) or what information or media is transmitted.

Functional programs and codes (code segments) for embodying the present invention may be easily inferred or modified by programmers in the art in considering system environments of computers reading storage media and executing programs.

The storage medium network-connected to the computer system may be distributed and computer-readable codes may be stored and executed in a distribution manner. In such case, at least one computer among a plurality of distributed computers may implement a portion of the functions and transmit results of the implementation to at least one computer that may also implement a portion of the functions and transmit results of the implementation to at least one computer.

The storage medium in which application (i.e., program) is recorded for executing the present invention includes a storage medium (e.g., hard disk) contained in application store servers or application provider servers, application provider servers per se, another computer having the program and its storage medium.

The computer system capable of reading the storage medium may include general PC such as desk top or notebook computers, mobile terminals such as Smartphone, Tablet PC, PDA (Personal Digital Assistants) and mobile communication terminals as well as all computing-executable devices.

The features and advantages of this invention will be summarized as follows:

(a) While the conventional methods detect abnormal signals using a single dataset, the present invention provides a novel approach to detect abnormal signals using a plurality of datasets obtained by a signal amplification reaction in a single reaction vessel.

(b) The present invention makes it possible to detect abnormal signals based on characteristics of abnormal signals commonly occurring in two or more datasets, which is useful in the multiplex detection method (e.g., multiplex PCR method).

(c) The present invention provides an opportunity to correct and eliminate an abnormal signal of one dataset using information about a cycle number indicative of an abnormal signal identified in another dataset.

(d) The method of the present invention can be implemented in a computer program to provide consistent and reproducible results.

(e) The method of the present invention can provide more accurate amplification curves and qualitative and quantitative information on a target analyte (in particular, a target nucleic acid sequence) by correcting or invalidating the abnormal signal determined by the present invention.

(f) The method of the present invention can remarkably reduce false positive or false negative results.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Detection of Abnormal Signals Using Individual Normality Score Approach Using an "intersection mode" as one of the individual normality score approaches of the present invention, it was verified whether abnormal signals could be detected in two or more datasets obtained from a real-time PCR reaction.

<1-1> Obtaining Datasets by Real-Time PCR Reactions

Samples were placed into different vessels for real-time PCR reactions. For each vessel, four datasets for four target nucleic acid sequences were obtained by a real-time PCR reaction using four different detection channels.

The real-time PCR reactions were performed on a CFX96™ Real-Time PCR Detection System (Bio-Rad Laboratories) with 45 cycles of amplification using a TaqMan probe as a signal-generating means.

For detection of the four target nucleic acid sequences, a probe labeled with a fluorescent reporter molecule FAM and a quencher molecule BHQ-1 (Black Hole Quencher), a probe labeled with CAL Fluor Orange 560 and BHQ-1, a probe labeled with CAL Fluor Red 610 and BHQ-2, a probe labeled with Quasar 670 and BHQ-2 were used, respectively.

Among the datasets obtained by the experiments, four datasets whose at least one dataset contained an abnormal signal(s) were selected for the individual normality score approach.

Figure 4:
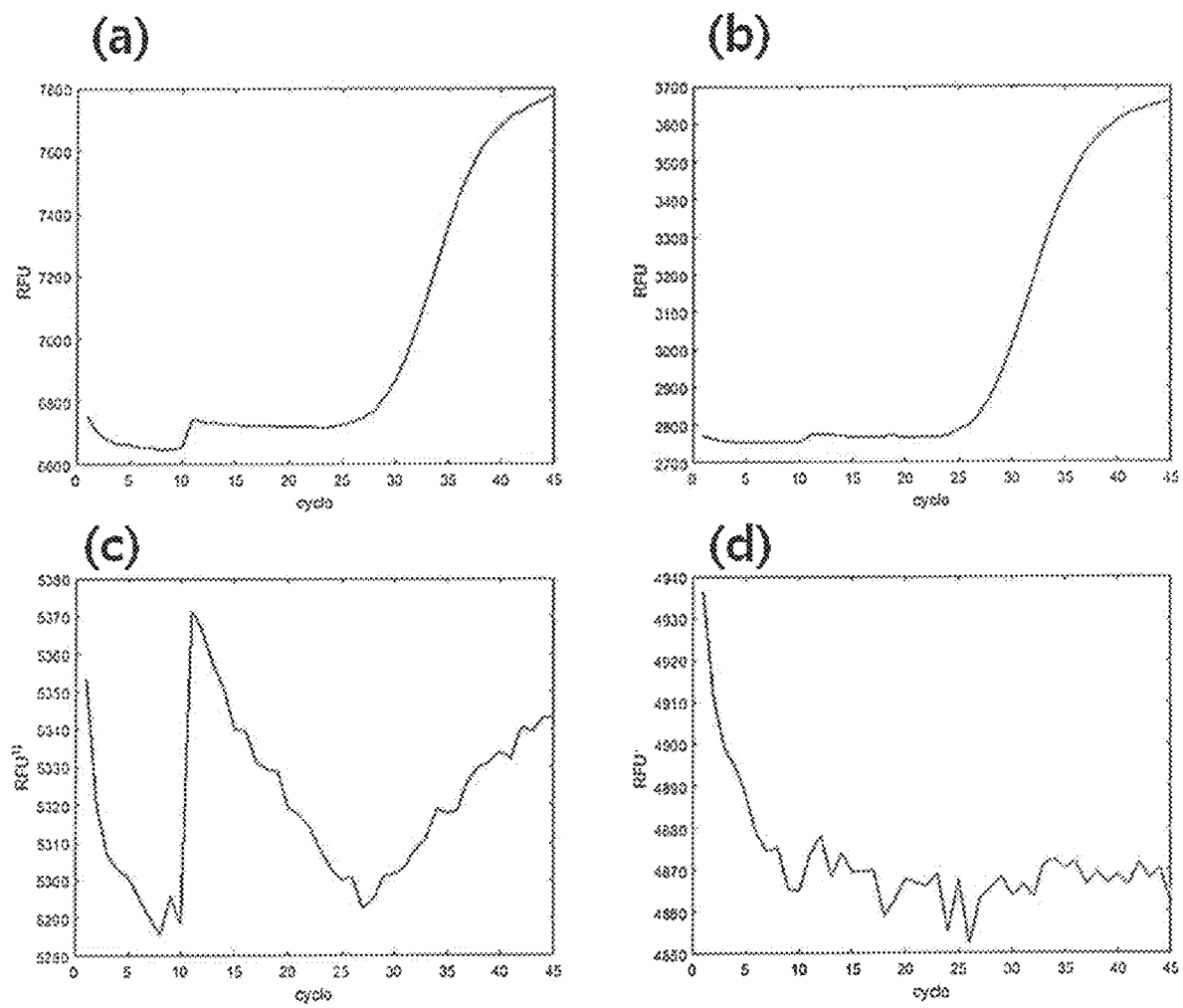
FIG. 4 represents datasets used in the analysis of Example 1, which were obtained by detection using four detection channels ((a): FAM; (b): CAL Fluor Orange 560; (c): CAL Fluor Red 610; (d) Quasar 670).

The amplification curves (a)-(d) representing four datasets for target nucleic acid sequences, obtained by the four different detection channels during the real-time PCR reaction, are shown in FIG. 4.

<1-2> Calculating Second-Order Difference at Each Cycle Number

For each dataset, the first-order difference at each cycle number was calculated by subtracting the signal values at two immediately adjacent cycle numbers. Then, the second-order difference at each cycle number was calculated by subtracting the first-order differences at two immediately adjacent cycle numbers. The calculation of the first-order differences and the second-order differences was performed by a backward difference method.

Specifically, the second-order difference at each cycle number was calculated using the following Equations IV and V sequentially or by using the following Equation VI alone.

$$D'_i(x) = y_j(x) - y_i(x-1) \qquad \text{Equation IV}$$

$$D''_i(x) = D'_i(x) - D'_i(x-1) \qquad \text{Equation V}$$

$$D''_i(x) = y_j(x) - 2*y_i(x-1) + y_i(x-2) \qquad \text{Equation VI}$$

wherein $D'_i(x)$ represents the first-order difference at the $x^{th}$ cycle number in the $i^{th}$ dataset; $D''_i(x)$ represents the second-order difference at the $x^{th}$ cycle number in the $i^{th}$ dataset; $y_i(x)$ is the signal value at the $x^{th}$ cycle number in the $i^{th}$ dataset; $y_i(x-1)$ is the signal value at the X' $i^{th}$ cycle number in the $i^{th}$ dataset; and $y_i(x-2)$ represents the signal value at the $x-2^{th}$ cycle number in the $i^{th}$ dataset.

<1-3> Calculating Normality Score (NS) at Each Cycle Number

Afterwards, the normality score (NS) at each cycle number was calculated by multiplying the second-order differences at two immediately adjacent cycle numbers, in accordance with the following Equation VII.

$$NS_i(x) = D''_i(x) * D''_i(x+1) \qquad \text{Equation VII}$$

wherein $NS_i(x)$ represents the normality score at the $x^{th}$ cycle number in the $i^{th}$ dataset; $D''_i(x)$ represents the second-order difference at the $x^{th}$ cycle number in the $i^{th}$ dataset; and $D''_i(x+1)$ represents the second-order difference at the $X+1^{th}$ cycle number in the $i^{th}$ dataset.

Figure 5:
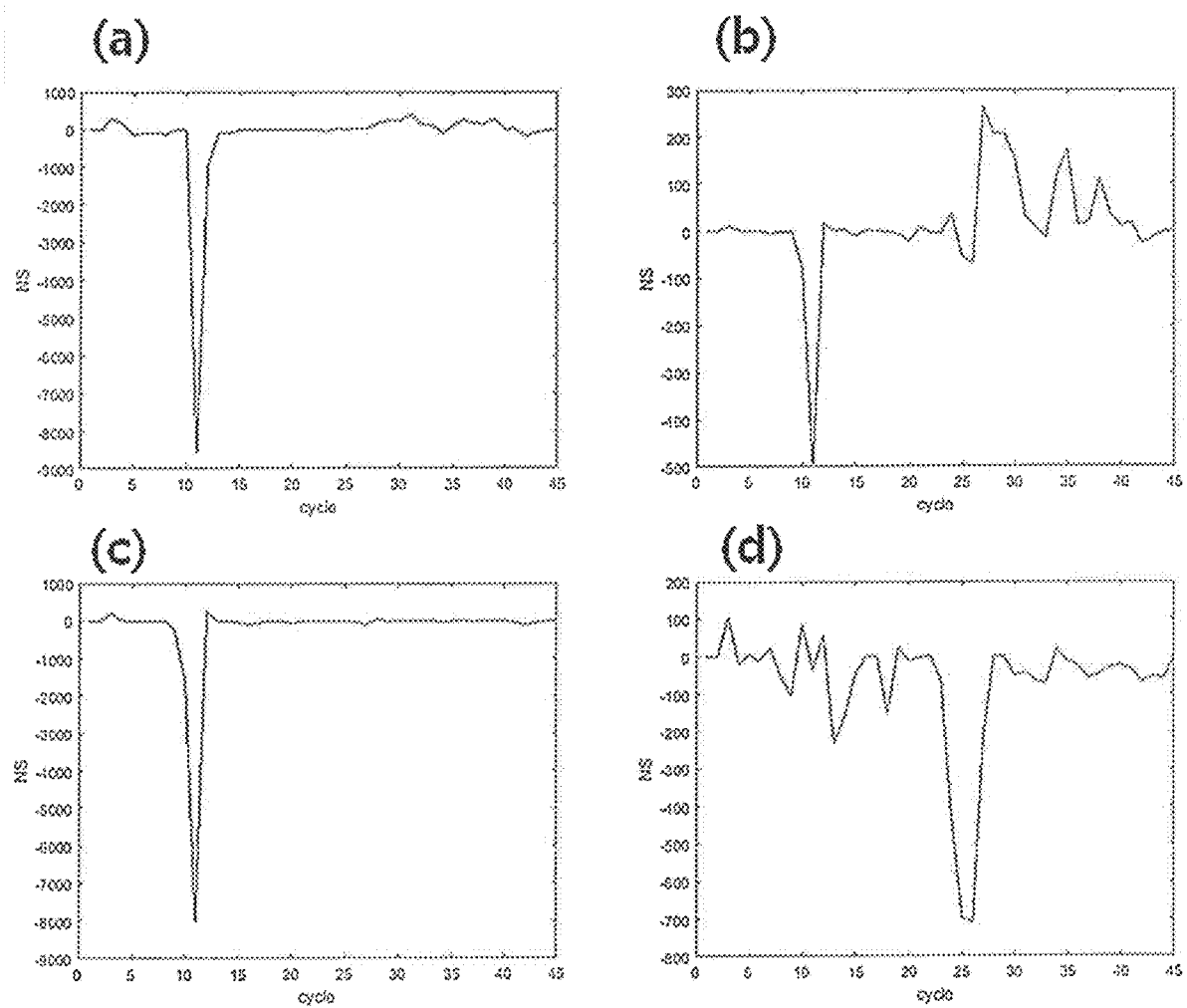
FIG. 5 is a schematic representation of normality scores (NS) calculated at each cycle number for the datasets (a)-(d) of FIG. 4.

The NS at each cycle number as calculated above is depicted in FIG. 5. The plots (a)-(d) represent the NS calculated at each cycle number for the datasets obtained by detection using each detection channel.

The NS at each cycle number for four datasets is shown in Table 1 below.

TABLE 1

| | x | | | | | | | | | |
|---|---|---|---|---|---|---|---|---|---|---|
| | 1 | 2 | 3 | 4 | 5 | 6 | 7 | 8 | 9 | 10 |
| $NS_1(x)$ | 0 | 0 | 295.83 | 140.68 | −132.69 | −82.05 | −79.68 | −131.23 | −4.00 | −23.88 |
| $NS_2(x)$ | 0 | 0 | 10.70 | 1.94 | 0.07 | 0.46 | −5.45 | −0.98 | −1.77 | −79.43 |
| $NS_3(x)$ | 0 | 0 | 197.53 | 10.50 | −3.15 | −0.69 | 0.14 | 8.71 | −257.43 | −1578.75 |
| $NS_4(x)$ | 0 | 0 | 104.83 | −18.10 | 5.46 | −11.10 | 23.83 | −53.52 | −102.58 | 85.74 |

| | x | | | | | | | | | |
|---|---|---|---|---|---|---|---|---|---|---|
| | 11 | 12 | 13 | 14 | 15 | 16 | 17 | 18 | 19 | 20 |
| $NS_1(x)$ | −8554.52 | −941.51 | −92.59 | −93.05 | −20.49 | −2.11 | 2.17 | −10.46 | −11.40 | 3.08 |
| $NS_2(x)$ | −496.01 | 17.60 | 0.91 | 2.34 | −9.79 | 2.33 | −0.60 | −1.36 | −6.25 | −21.90 |
| $NS_3(x)$ | −8002.29 | 248.35 | −5.57 | −8.60 | −45.92 | −87.64 | −54.53 | 9.41 | −13.38 | −77.80 |
| $NS_4(x)$ | −34.00 | 56.26 | −231.06 | −157.55 | −46.82 | 0.09 | −0.21 | −152.94 | 25.10 | −11.29 |

| | x | | | | | | | | | |
|---|---|---|---|---|---|---|---|---|---|---|
| | 21 | 22 | 23 | 24 | 25 | 26 | 27 | 28 | 29 | 30 |
| $NS_1(x)$ | 1.79 | −8.74 | −55.06 | 11.98 | 6.58 | 15.52 | 26.09 | 171.18 | 226.62 | 215.72 |
| $NS_2(x)$ | 7.78 | −4.02 | −4.99 | 34.28 | −55.63 | −68.12 | 263.62 | 207.41 | 206.18 | 153.84 |
| $NS_3(x)$ | −15.29 | 4.79 | −2.16 | 1.83 | 8.43 | −35.67 | −98.35 | 44.41 | −24.98 | −9.36 |
| $NS_4(x)$ | −2.81 | 1.63 | −61.54 | −429.52 | −697.83 | −708.90 | −222.56 | −0.64 | −0.53 | −51.39 |

| | x | | | | | | | | | |
|---|---|---|---|---|---|---|---|---|---|---|
| | 31 | 32 | 33 | 34 | 35 | 36 | 37 | 38 | 39 | 40 |
| $NS_1(x)$ | 406.55 | 148.35 | 104.36 | −90.40 | 94.85 | 270.37 | 158.56 | 152.48 | 276.10 | 7.72 |
| $NS_2(x)$ | 31.22 | 4.84 | −14.98 | 116.26 | 173.74 | 12.35 | 18.71 | 110.72 | 36.98 | 11.96 |

TABLE 1-continued

| | | | | | | | | | | |
|---|---|---|---|---|---|---|---|---|---|---|
| $NS_3(x)$ | 4.10 | −3.72 | −6.04 | −36.18 | −17.16 | 13.69 | −28.60 | 8.17 | −1.95 | −4.37 |
| $NS_4(x)$ | −42.52 | −63.52 | −71.88 | 21.47 | −11.32 | −23.64 | −56.20 | −46.85 | −27.38 | −22.22 |

| | x | | | | | | | | | |
|---|---|---|---|---|---|---|---|---|---|---|
| | 41 | 42 | 43 | 44 | 45 | — | — | — | — | — |
| $NS_1(x)$ | 9.95 | −178.42 | −73.14 | −28.74 | 0 | — | — | — | — | — |
| $NS_2(x)$ | 17.14 | −27.52 | −12.95 | −2.24 | 0 | — | — | — | — | — |
| $NS_3(x)$ | −45.55 | −105.64 | −53.26 | −20.11 | 0 | — | — | — | — | — |
| $NS_4(x)$ | −35.81 | −69.03 | −50.34 | −58.11 | 0 | — | — | — | — | — |

<1-4> Selecting a Cycle Number Having a Minimum NS and Determining a Cycle Number Indicative of an Abnormal Signal According to Intersection Mode Based on the NS, a cycle number having a minimum NS for each dataset was selected.

The selected cycle numbers for each dataset and the NS at the selected cycle numbers are shown in Table 2 below.

TABLE 2

| | 1st dataset | 2nd dataset | 3rd dataset | 4th dataset |
|---|---|---|---|---|
| Selected cycle number | 11 | 11 | 11 | 26 |
| NS | −8554.52 | −496.01 | −8002.29 | −708.90 |

According to the intersection mode of the present invention, a cycle number commonly selected in 50% or more of all datasets was determined as a cycle number indicative of an abnormal signal.

As shown in Table 2 above, the cycle number 11 was commonly selected in the three (75%) out of a total of four datasets, and thus the cycle number 11 was finally determined as a cycle number indicative of an abnormal signal.

Example 2: Detection of Abnormal Signals Using Integrated Normality Score Approach Using a "Gap mode" as one of the integrated normality score approaches of the present invention, it was examined whether abnormal signals could be detected in two or more datasets obtained from a real-time PCR reaction.

<2-1> Obtaining Datasets by Real-Time PCR Reactions

In this Example, four datasets different from those of Example 1 were used for the integrated normality score approach.

Figure 6:
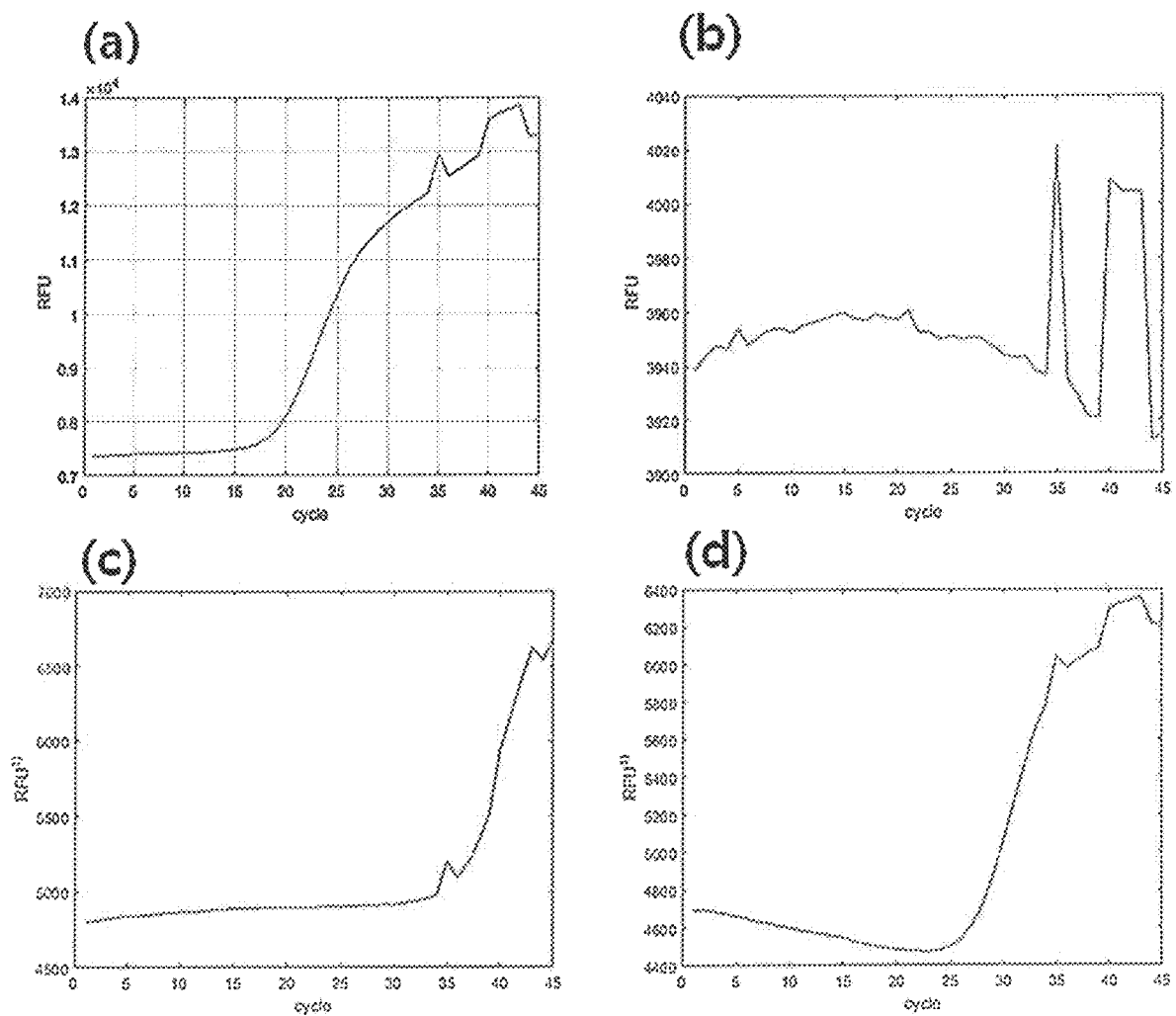
FIG. 6 represents datasets used in the analysis of Example 2, which were obtained by detection using four detection channels ((a): FAM; (b): CAL Fluor Orange 560; (c): CAL Fluor Red 610; (d) Quasar 670).

The amplification curves (a)-(d) representing datasets for target nucleic acid sequences, obtained by the four different detection channels during the real-time PCR reaction are shown in FIG. 6.

<2-2> Calculating Second-Order Difference at Each Cycle Number

For each dataset, the second-order difference at each cycle number was calculated as described in Example <1-2>.

<2-3> Calculating Normality Score (NS) at Each Cycle Number

For each dataset, the normality score (NS) at each cycle number was calculated as described in Example <1-3>.

Figure 7:
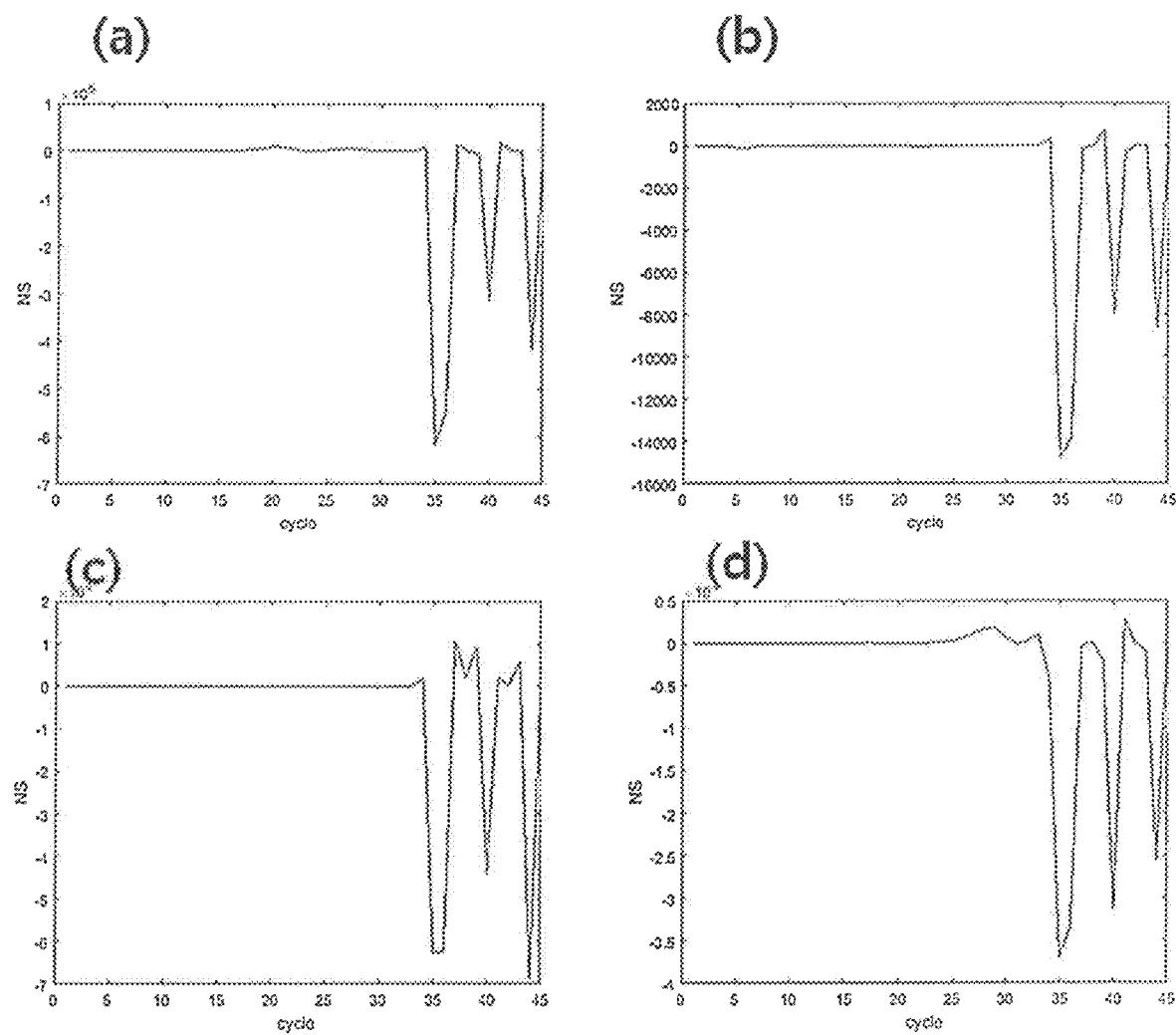
FIG. 7 is a schematic representation of normality scores (NS) calculated at each cycle number for the datasets (a)-(d) of FIG. 6.

The NS at each cycle number as calculated above is depicted in FIG. 7. The plots (a)-(d) represent the NS calculated at each cycle number for the datasets obtained by detection using each detection channel.

The NS at each cycle number for four datasets is shown in Table 3.

TABLE 3

| | x | | | | | | | | | |
|---|---|---|---|---|---|---|---|---|---|---|
| | 1 | 2 | 3 | 4 | 5 | 6 | 7 | 8 | 9 | 10 |
| $NS_1(x)$ | 0 | 0 | −244.9 | −52.5 | 2.6 | −7.3 | −17.8 | 12.2 | −13.9 | 2.0 |
| $NS_2(x)$ | 0 | 0 | 3.3 | −40.0 | −107.6 | −127.3 | −13.7 | 2.0 | 3.3 | −10.4 |
| $NS_3(x)$ | 0 | 0 | −3.8 | −0.8 | 5.5 | −24.3 | 18.7 | −40.8 | 7.9 | 4.8 |
| $NS_4(x)$ | 0 | 0 | −21.6 | −2.6 | −4.9 | −16.1 | −77.4 | −116.6 | −72.9 | −29.3 |

| | x | | | | | | | | | |
|---|---|---|---|---|---|---|---|---|---|---|
| | 11 | 12 | 13 | 14 | 15 | 16 | 17 | 18 | 19 | 20 |
| $NS_1(x)$ | −7.2 | −2.4 | −1.0 | 25.0 | 56.4 | 177.0 | 1410.6 | 3159.2 | 5383.0 | 10090.1 |
| $NS_2(x)$ | −6.7 | −0.1 | 0.0 | −0.2 | 2.1 | −6.0 | 4.7 | −7.8 | −1.3 | 1.6 |
| $NS_3(x)$ | −17.6 | 10.8 | −16.4 | −98.0 | −119.6 | 22.2 | −11.4 | −13.0 | 12.8 | −45.1 |
| $NS_4(x)$ | −29.6 | −26.8 | −5.4 | 1.5 | −13.4 | −86.5 | 23.3 | 2.2 | 2.1 | 2.0 |

| | x | | | | | | | | | |
|---|---|---|---|---|---|---|---|---|---|---|
| | 21 | 22 | 23 | 24 | 25 | 26 | 27 | 28 | 29 | 30 |
| $NS_1(x)$ | 8110.6 | 3756.5 | −333.9 | 268.1 | 2071.9 | 3413.2 | 5654.1 | 3053.7 | 1452.1 | 1169.1 |
| $NS_2(x)$ | −45.3 | −85.8 | −18.2 | −9.1 | −8.8 | −3.8 | −1.5 | 2.6 | −1.4 | 0.9 |
| $NS_3(x)$ | −63.0 | −54.0 | −19.0 | 12.8 | −39.1 | −16.7 | 8.1 | −39.5 | −133.3 | −220.8 |
| $NS_4(x)$ | 1.6 | 4.9 | 16.7 | 108.0 | 199.5 | 627.2 | 1136.0 | 1594.7 | 1798.6 | 593.4 |

TABLE 3-continued

| | x | | | | | | | | | |
|---|---|---|---|---|---|---|---|---|---|---|
| | 31 | 32 | 33 | 34 | 35 | 36 | 37 | 38 | 39 | 40 |
| $NS_1(x)$ | 24.2 | 16.4 | −303.0 | 9294.0 | −616570.9 | −549033.5 | 14112.2 | −344.2 | −6773.6 | −313687.8 |
| $NS_2(x)$ | 2.2 | −6.8 | −20.5 | 320.3 | −14789.7 | −13842.3 | −141.7 | −13.7 | 680.5 | −7968.2 |
| $NS_3(x)$ | −65.3 | −22.6 | 57.1 | 1883.1 | −62601.6 | −62323.7 | 10500.2 | 2091.0 | 9329.3 | −44045.2 |
| $NS_4(x)$ | −140.5 | 214.0 | 964.5 | −4078.4 | −36992.8 | −33397.6 | −309.9 | 33.9 | −2048.4 | −31352.8 |

| | x | | | | | | | | | |
|---|---|---|---|---|---|---|---|---|---|---|
| | 41 | 42 | 43 | 44 | 45 | — | — | — | — | — |
| $NS_1(x)$ | 19965.0 | 106.3 | 1976.5 | −417636.9 | 0 | — | — | — | — | — |
| $NS_2(x)$ | −326.8 | 1.6 | −41.6 | −8637.2 | 0 | — | — | — | — | — |
| $NS_3(x)$ | 2041.9 | 212.8 | 5668.8 | −68608.1 | 0 | — | — | — | — | — |
| $NS_4(x)$ | 2656.4 | −94.5 | −1043.7 | −25553.5 | 0 | — | — | — | — | — |

<2-4> Assigning Ranking Score (RS)

For each dataset, a ranking score (RS) was assigned to each cycle number according to the magnitude of the NS. The assignment of RS was performed such that a smaller RS was assigned to a cycle number having a smaller NS, starting from RS "1".

<2-5> Calculating Total Ranking Score (TRS)

Afterwards, the RS assigned to the same cycle number was summed for all datasets to obtain the total ranking score (TRS) at each cycle number.

The TRS obtained thus at each cycle number is shown in Table 4.

In the table, $RS_1(x)$ to $RS_4(x)$ represent RS at the $x^{th}$ cycle number in the $1^{st}$ to $4^{th}$ datasets, respectively; and $TRS(x)$ represents TRS obtained by summing the RSs at the $x^{th}$ cycle number.

According to the present method, the NS, the RS, and the TRS at the $1^{st}$ and $2^{nd}$ cycle numbers are not calculated, because the second-order difference is calculated by the backward difference method. Further, the NS, the RS, and the TRS at the $45^{th}$ cycle number are not calculated, because the NS is calculated by Equation VII.

<2-6> Determining a Cycle Number Indicative of an Abnormal Signal by Identification of a Largest Gap The total ranking scores (TRS) at all cycle numbers were arranged in ascending order. The results are shown in Table 5.

TABLE 4

| | x | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| $RS_1(x)$ | — | — | 9 | 10 | 18 | 13 | 11 | 19 | 12 | 17 | 14 | 15 | 16 | 22 | 23 |
| $RS_2(x)$ | — | — | 38 | 12 | 8 | 7 | 16 | 34 | 39 | 17 | 22 | 29 | 30 | 28 | 35 |
| $RS_3(x)$ | — | — | 24 | 25 | 27 | 16 | 33 | 13 | 28 | 26 | 19 | 30 | 21 | 8 | 7 |
| $RS_4(x)$ | — | — | 18 | 23 | 22 | 19 | 13 | 10 | 14 | 16 | 15 | 17 | 21 | 24 | 20 |
| $TRS(x)$ | — | — | 89 | 70 | 75 | 55 | 73 | 76 | 93 | 76 | 70 | 91 | 88 | 82 | 85 |

| | x | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| $RS_1(x)$ | 25 | 28 | 33 | 36 | 40 | 38 | 35 | 7 | 26 | 31 | 34 | 37 | 32 | 29 | 27 |
| $RS_2(x)$ | 23 | 40 | 20 | 27 | 33 | 10 | 9 | 14 | 18 | 19 | 24 | 25 | 37 | 26 | 31 |
| $RS_3(x)$ | 34 | 23 | 22 | 32 | 12 | 10 | 11 | 18 | 31 | 15 | 20 | 29 | 14 | 6 | 5 |
| $RS_4(x)$ | 12 | 31 | 28 | 27 | 26 | 25 | 29 | 30 | 33 | 34 | 37 | 39 | 40 | 41 | 36 |
| $TRS(x)$ | 94 | 122 | 103 | 122 | 111 | 83 | 84 | 69 | 108 | 99 | 115 | 130 | 123 | 102 | 99 |

| | x | | | | | | | | | | | | | | |
|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 |
| $RS_1(x)$ | 21 | 20 | 8 | 39 | 1 | 2 | 41 | 6 | 5 | 4 | 42 | 24 | 30 | 3 | — |
| $RS_2(x)$ | 36 | 21 | 13 | 41 | 1 | 2 | 6 | 15 | 42 | 4 | 5 | 32 | 11 | 3 | — |
| $RS_3(x)$ | 9 | 17 | 35 | 37 | 2 | 3 | 42 | 39 | 41 | 4 | 38 | 36 | 40 | 1 | — |
| $RS_4(x)$ | 9 | 35 | 38 | 5 | 1 | 2 | 8 | 32 | 6 | 3 | 42 | 11 | 7 | 4 | — |
| $TRS(x)$ | 75 | 93 | 94 | 122 | 5 | 9 | 97 | 92 | 94 | 15 | 127 | 103 | 88 | 11 | — |

TABLE 5

| | x | | | | | | | | | | | | | |
|---|---|---|---|---|---|---|---|---|---|---|---|---|---|---|
| | 35 | 36 | 44 | 40 | 6 | 23 | 4 | 11 | 7 | 5 | 31 | 8 | 10 | 14 | 21 |
| TRS(x) | 5 | 9 | 11 | 15 | 55 | 69 | 70 | 70 | 73 | 75 | 75 | 76 | 76 | 82 | 83 |
| | x | | | | | | | | | | | | | |
| | 22 | 15 | 13 | 43 | 3 | 12 | 38 | 9 | 32 | 16 | 33 | 39 | 37 | 25 | 30 |
| TRS(x) | 84 | 85 | 88 | 88 | 89 | 91 | 92 | 93 | 93 | 94 | 94 | 94 | 97 | 99 | 99 |
| | x | | | | | | | | | | | | | |
| | 29 | 18 | 42 | 24 | 20 | 26 | 17 | 19 | 34 | 28 | 41 | 27 | — | — | — |
| TRS(x) | 102 | 103 | 103 | 108 | 111 | 115 | 122 | 122 | 122 | 123 | 127 | 130 | — | — | — |

In order to facilitate the analysis, the TRS was arranged one-dimensionally. In the arrangement, the TRS was positioned at its coordinate corresponding to its magnitude. For accurate determination of the largest gap (outlier gap), a reference total ranking score "0" was additionally introduced into the arrangement. The reference total ranking score "0" as a minimum total ranking score was obtained by further introducing a reference ranking score "0" for each dataset according the scoring system of ranking score and summing the reference ranking scores of all datasets.

Figure 8:
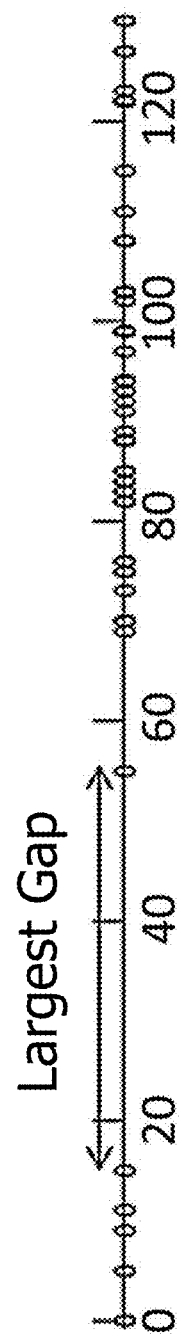
FIG. 8 represents one-dimensional arrangement of total ranking scores (TRS) for the datasets (a)-(d) of FIG. 6, according to the magnitude of the TRS. In the arrangement, the minimum TRS 0 is additionally inserted and the largest gap is indicated.

The result of one-dimensional arrangement of the TRS according to its magnitude is shown in FIG. 8.

In this arrangement, a gap between two neighboring TRS was calculated, and the largest gap (outlier gap) was then identified. As seen from FIG. 8 and Table 5, the gap between TRS 15 at cycle number 40 and TRS 55 at cycle number 6 was identified as the largest gap.

According to the Gap mode embodied in this Example, a TRS smaller than or equal to a relatively small TRS out of two neighboring TRS of the largest gap was identified as an outlier, and a cycle number of the outlier was determined as a cycle number indicative of an abnormal signal. In this Example, the cycle numbers of 35, 36, 44 and 40 corresponding to TRS 5, 9, 11 and 15, respectively, were determined as a cycle number indicative of an abnormal signal.

Example 3: Detection of Abnormal Signals Using a Combination of Gap Mode and Intersection Mode By using a combination of the "Gap mode" and the "intersection mode" of the present invention, it was verified whether abnormal signals could be detected in two or more datasets obtained from a real-time PCR reaction.

<3-1> Obtaining Datasets by Real-Time PCR Reactions

In this Example, four datasets different from those of Examples 1 and 2 were used for data analysis.

Figure 9:
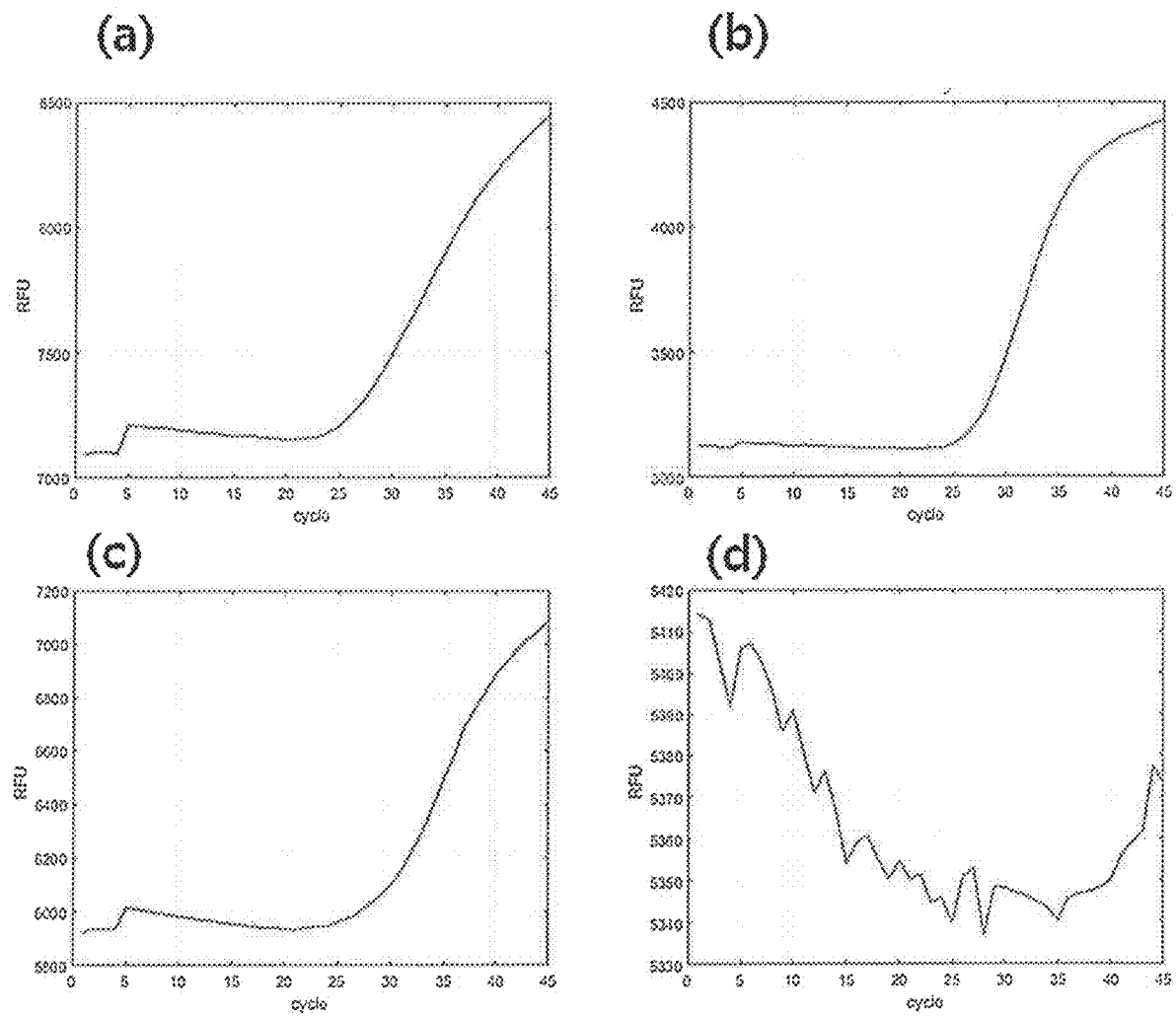
FIG. 9 represents datasets used in the analysis of Example 3, which were obtained by detection using four detection channels ((a): FAM; (b): CAL Fluor Orange 560; (c): CAL Fluor Red 610; (d) Quasar 670).

The amplification curves (a)-(d) representing datasets for target nucleic acid sequences, obtained by the four different detection channels during the real-time PCR reaction are shown in FIG. 9.

<3-2> Calculating Second-Order Difference at Each Cycle Number

The second-order difference at each cycle number was calculated as described in Example <1-2>.

<3-3> Calculating Normality Score (NS) at Each Cycle Number

Figure 10:
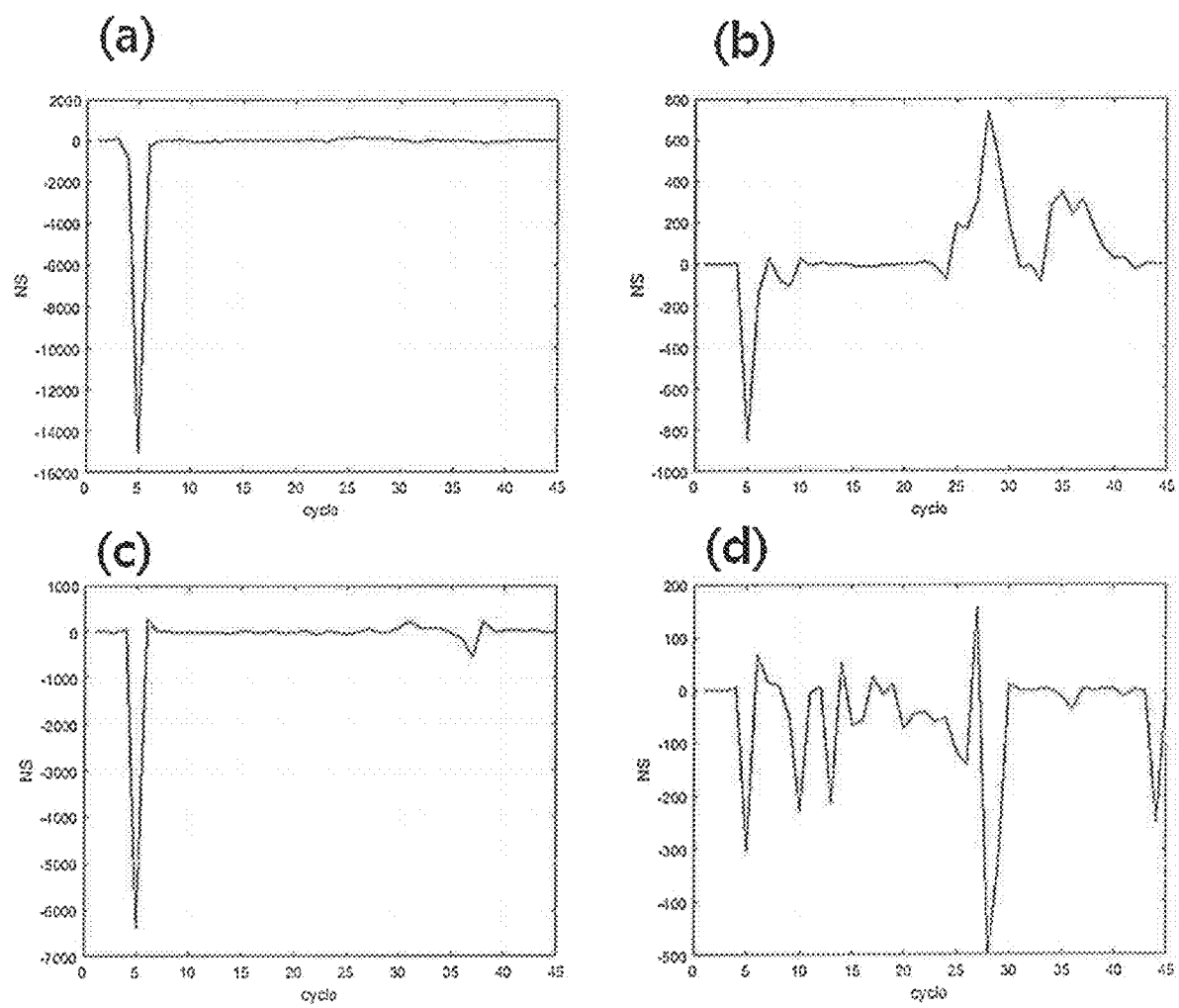
FIG. 10 is a schematic representation of normality scores (NS) calculated at each cycle number for the datasets (a)-(d) of FIG. 9.

The normality score (NS) at each cycle number was calculated as described in Example <1-3>. The NS calculated at each cycle number is shown in FIG. 10. The NS at each cycle number for four datasets is shown in Table 6.

TABLE 6

| | x | | | | | | | | | |
|---|---|---|---|---|---|---|---|---|---|---|
| | 1 | 2 | 3 | 4 | 5 | 6 | 7 | 8 | 9 | 10 |
| $NS_1(x)$ | 0 | 0 | 82.70 | −906.84 | −15063.61 | −266.80 | 4.35 | −5.76 | 18.38 | −53.89 |
| $NS_2(x)$ | 0 | 0 | −0.47 | 4.62 | −851.85 | −140.75 | 27.50 | −79.79 | −105.40 | 25.30 |
| $NS_3(x)$ | 0 | 0 | −9.24 | 50.19 | −6382.69 | 272.39 | −0.77 | 0.92 | −17.02 | −18.88 |
| $NS_4(x)$ | 0 | 0 | −1.57 | 4.26 | −302.86 | 67.54 | 13.95 | 8.52 | −49.31 | −229.63 |
| | x | | | | | | | | | |
| | 11 | 12 | 13 | 14 | 15 | 16 | 17 | 18 | 19 | 20 |
| $NS_1(x)$ | −52.39 | −45.79 | −47.63 | 1.02 | −1.25 | −28.38 | 6.79 | −1.47 | −1.26 | −12.65 |
| $NS_2(x)$ | −6.86 | 8.18 | −6.14 | 4.25 | −8.68 | −12.49 | −9.32 | −7.49 | −7.88 | 1.83 |
| $NS_3(x)$ | −15.80 | −15.37 | −25.60 | −26.97 | 4.51 | −3.01 | −9.45 | 14.20 | −28.43 | −16.81 |
| $NS_4(x)$ | −5.19 | 5.11 | −213.02 | 53.14 | −66.16 | −59.06 | 24.30 | −8.77 | 10.42 | −73.16 |
| | x | | | | | | | | | |
| | 21 | 22 | 23 | 24 | 25 | 26 | 27 | 28 | 29 | 30 |
| $NS_1(x)$ | 24.60 | −12.86 | −70.08 | 88.03 | 85.46 | 147.60 | 68.68 | 93.96 | 65.75 | 39.68 |
| $NS_2(x)$ | −2.48 | 9.88 | −11.93 | −74.69 | 192.87 | 168.99 | 309.72 | 738.00 | 493.12 | 189.67 |

TABLE 6-continued

| | | | | | | | | | | |
|---|---|---|---|---|---|---|---|---|---|---|
| $NS_3(x)$ | 27.76 | −71.20 | 4.31 | −10.83 | −54.21 | −16.74 | 68.32 | −13.86 | −9.63 | 97.95 |
| $NS_4(x)$ | −45.49 | −41.94 | −59.80 | −52.93 | −115.16 | −142.81 | 156.07 | −499.94 | −321.95 | 9.92 |

| | x | | | | | | | | | |
|---|---|---|---|---|---|---|---|---|---|---|
| | 31 | 32 | 33 | 34 | 35 | 36 | 37 | 38 | 39 | 40 |
| $NS_1(x)$ | −49.88 | −58.22 | 26.20 | −29.80 | −17.11 | −20.87 | −70.74 | −110.07 | −79.87 | −52.04 |
| $NS_2(x)$ | −18.60 | −8.48 | −86.19 | 284.52 | 344.42 | 238.36 | 310.55 | 182.22 | 73.97 | 23.41 |
| $NS_3(x)$ | 223.87 | 82.97 | 76.01 | 73.78 | −35.56 | −142.03 | −537.57 | 224.08 | 9.80 | 23.31 |
| $NS_4(x)$ | −0.45 | −0.33 | 0.11 | 0.29 | −13.89 | −38.68 | 1.98 | −0.25 | 0.32 | 2.46 |

| | x | | | | |
|---|---|---|---|---|---|
| | 41 | 42 | 43 | 44 | 45 |
| $NS_1(x)$ | −33.29 | −18.53 | 3.95 | 2.04 | 0 |
| $NS_2(x)$ | 28.19 | −28.97 | 1.21 | −3.06 | 0 |
| $NS_3(x)$ | 29.60 | 15.47 | 29.57 | −22.45 | 0 |
| $NS_4(x)$ | −13.24 | 0.95 | −4.03 | −250.02 | 0 |

<3-4> Assigning Ranking Score (RS)

The ranking score (RS) was assigned to at each cycle number as described in Example <1-4>. The RS assigned to each cycle number is shown in Table 7.

<3-5> Calculating Total Ranking Score (TRS)

The total ranking score (TRS) at each cycle number was calculated as described in Example <2-5>. The TRS calculated at each cycle number is shown in Table 7.

TABLE 7

| | x | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| $RS_1(x)$ | — | — | 38 | 2 | 1 | 3 | 30 | 23 | 32 | 9 | 10 | 14 | 13 | 27 | 26 |
| $RS_2(x)$ | — | — | 20 | 24 | 1 | 2 | 29 | 5 | 3 | 28 | 16 | 25 | 17 | 23 | 12 |
| $RS_3(x)$ | — | — | 21 | 34 | 1 | 42 | 23 | 24 | 12 | 11 | 15 | 16 | 9 | 8 | 26 |
| $RS_4(x)$ | — | — | 23 | 33 | 3 | 41 | 38 | 35 | 14 | 5 | 21 | 34 | 6 | 40 | 10 |
| TRS(x) | — | — | 102 | 93 | 6 | 88 | 120 | 87 | 61 | 53 | 62 | 89 | 45 | 98 | 74 |

| | x | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| $RS_1(x)$ | 17 | 31 | 24 | 25 | 22 | 33 | 21 | 7 | 40 | 39 | 42 | 37 | 41 | 36 | 35 |
| $RS_2(x)$ | 9 | 11 | 15 | 14 | 22 | 19 | 26 | 10 | 6 | 35 | 32 | 38 | 42 | 41 | 34 |
| $RS_3(x)$ | 22 | 20 | 28 | 7 | 13 | 31 | 4 | 25 | 18 | 5 | 14 | 35 | 17 | 19 | 39 |
| $RS_4(x)$ | 12 | 39 | 20 | 37 | 9 | 15 | 16 | 11 | 13 | 8 | 7 | 42 | 1 | 2 | 36 |
| TRS(x) | 60 | 101 | 87 | 83 | 66 | 98 | 67 | 53 | 77 | 87 | 95 | 152 | 101 | 98 | 144 |

| | x | | | | | | | | | | | | | | |
|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 |
| $RS_1(x)$ | 12 | 8 | 34 | 16 | 20 | 18 | 6 | 4 | 5 | 11 | 15 | 19 | 29 | 28 | — |
| $RS_2(x)$ | 8 | 13 | 4 | 37 | 40 | 36 | 39 | 33 | 31 | 27 | 30 | 7 | 21 | 18 | — |
| $RS_3(x)$ | 40 | 38 | 37 | 36 | 6 | 3 | 2 | 41 | 27 | 30 | 33 | 29 | 32 | 10 | — |
| $RS_4(x)$ | 24 | 25 | 27 | 28 | 18 | 17 | 31 | 26 | 29 | 32 | 19 | 30 | 22 | 4 | — |
| TRS(x) | 84 | 84 | 102 | 117 | 84 | 74 | 78 | 104 | 92 | 100 | 97 | 85 | 104 | 60 | — |

<3-6> Determining a Cycle Number Indicative of an Abnormal Signal by Identification of a Largest Gap The total ranking scores (TRS) were arranged in ascending order. The result is shown in Table 8.

TABLE 8

| x | | | | | | | | | | | | | |
|---|---|---|---|---|---|---|---|---|---|---|---|---|---|
| 5 | 13 | 10 | 23 | 16 | 44 | 9 | 11 | 20 | 22 | 15 | 36 | 24 | 37 |
| TRS(x) | | | | | | | | | | | | | |
| 6 | 45 | 53 | 53 | 60 | 60 | 61 | 62 | 66 | 67 | 74 | 74 | 77 | 78 |

| x | | | | | | | | | | | | | |
|---|---|---|---|---|---|---|---|---|---|---|---|---|---|
| 19 | 31 | 32 | 35 | 42 | 8 | 18 | 25 | 6 | 12 | 39 | 4 | 26 | 41 |
| TRS(x) | | | | | | | | | | | | | |
| 83 | 84 | 84 | 84 | 85 | 87 | 87 | 87 | 88 | 89 | 92 | 93 | 95 | 97 |

| x | | | | | | | | | | | | | |
|---|---|---|---|---|---|---|---|---|---|---|---|---|---|
| 14 | 21 | 29 | 40 | 17 | 28 | 3 | 33 | 38 | 43 | 34 | 7 | 30 | 27 |
| TRS(x) | | | | | | | | | | | | | |
| 98 | 98 | 98 | 100 | 101 | 101 | 102 | 102 | 104 | 104 | 117 | 120 | 144 | 152 |

In order to facilitate the analysis, the TRS was arranged one-dimensionally. In the arrangement, each TRS was positioned at its coordinate corresponding to its size. For accurate determination of the largest gap (outlier gap), a reference total ranking score "0" was additionally introduced into the arrangement. The reference total ranking score "0" as a minimum total ranking score was obtained by further introducing a reference ranking score "0" for each dataset according the scoring system of ranking score and summing the reference ranking scores of all datasets.

The result of one-dimensional arrangement of the TRS according to its size is shown in FIG. 11.

In this arrangement, a gap between two neighboring TRS was calculated, and the largest gap (outlier gap) was then identified. As seen from FIG. 11 and Table 6, the gap between TRS 6 corresponding to cycle number 5 and TRS 45 corresponding to cycle number 13 was identified as the largest gap.

According to the Gap mode embodied in this Example, the cycle number of 5 corresponding to TRS 6 was determined as a cycle number indicative of an abnormal signal.

<3-7> Determining a Cycle Number Indicative of an Abnormal Signal by the Intersection Mode The same datasets used in the Gap mode was again used to determine a cycle number indicative of an abnormal signal according to the intersection mode.

The intersection mode was performed in the same manner as described in Example 1.

The selected cycle numbers for each dataset and the NS at the selected cycle numbers are shown in Table 9.

TABLE 9

|  | 1st dataset | 2nd dataset | 3rd dataset | 4th dataset |
|---|---|---|---|---|
| Selected cycle number | 5 | 5 | 5 | 28 |
| NS | −15063.6 | −851.8 | −6382.7 | −499.9 |

As shown in Table 9 above, the cycle number 5 was commonly selected in three out of the four datasets (75%), and thus the cycle number 5 was finally determined as a cycle number indicative of an abnormal signal.

The cycle number determined by the intersection mode in the Example <3-7> was identical to that determined by the Gap mode in the Example <3-6>. Accordingly, it was verified that the cycle number 5 is a cycle number indicative of an abnormal signal.

The above results demonstrate that a combination of the modes according to the present invention allows for determination of cycle numbers indicative of abnormal signals in a more accurate manner. The results also demonstrate that the Gap mode and the intersection mode may be used separately or in combination.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting an abnormal signal using two or more datasets, comprising:
    (a) obtaining two or more datasets by a signal amplification reaction in a single reaction vessel; wherein each of the datasets comprises a plurality of data points; wherein each of the data points has a cycle number and a signal value at the cycle number;
    (b) calculating a second-order change value at each cycle number of each dataset;
    (c) calculating a normality score at each cycle number of each dataset by using the second-order change value; wherein the calculation of the normality score is performed by a mathematical operation that represents sign change between and magnitudes of the second-order change values at two consecutive cycle numbers; and
    (d) determining a cycle number indicative of an abnormal signal by using the normality score.

2. The method of claim 1,
    wherein the calculation of the second-order change value in the step (b) is performed by calculating a first-order change value at each cycle number of each dataset by using two signal values at two consecutive cycle numbers, and then calculating a second-order change value at each cycle number of each dataset by using the two first-order change values at two consecutive cycle numbers.

3. The method of claim 1, wherein the second-order change value in the step (b) is any one selected from the group consisting of a second-order difference, a second-order difference quotient, and a second-order derivative.

4. The method of claim 3, wherein the second-order difference or a second-order difference quotient is obtained by a forward or backward difference method.

5. The method of claim 1, wherein the calculation of the normality score in the step (c) is performed by multiplying the second-order change values at two consecutive cycle numbers.

6. The method of claim 5, wherein the calculation of the normality score in the step (c) is performed by the following Equations VII or VIII:

$$NSi(x)=D''i(x)*D''i(x+1) \qquad \text{Equation VII}$$

wherein NSi(x) represents a normality score at the xth cycle number of the ith dataset, D''i(x) represents a second-order change value at the xth cycle number of the ith dataset, D''i(x+1) represents a second-order change value at the (x+1)th cycle number of the ith dataset, and i and x are each integer of 1 or more;

$$NSi(x)=D''i(x)*D''i(x-1) \qquad \text{Equation VIII}$$

wherein NSi(x) represents a normality score at the xth cycle number of the ith dataset, D''i(x) represents a second-order change value at the xth cycle number of the ith dataset, D''i(x−1) represents a second-order change value at the (x−1)th cycle number of the ith dataset, and i and x are each integer of 1 or more.

7. The method of claim 1, wherein the step (d) is performed by comparing the normality score to a threshold, wherein the threshold is selected from values less than 0;
 selecting a cycle number having a normality score smaller than the threshold for each dataset;
 and determining all or a portion of the selected cycle numbers as a cycle number indicative of an abnormal signal for each dataset.

8. The method of claim 1, wherein the step (d) is performed by comparing the normality score to a threshold, wherein the threshold is selected from values less than 0;
 selecting a cycle number having a normality score which is smaller than the threshold and is the minimum for each dataset, and determining all or a portion of the selected cycle numbers as a cycle number indicative of an abnormal signal for all each dataset.

9. The method of claim 1, wherein the step (d) is performed by selecting a cycle number having a minimum normality score for each dataset, and determining all or a portion of the selected cycle numbers as a cycle number indicative of an abnormal signal for each datasets.

10. The method of claim 1, wherein the step (d) comprises the following sub-steps:
 (d-1) assigning a ranking score to each cycle number of each dataset according to the magnitude of its normality score;
 (d-2) summing or multiplying the ranking scores assigned to the same cycle number of each dataset, to obtain a total ranking score at each cycle number;
 (d-3) identifying an outlier(s) among the total ranking scores; and
 (d-4) determining a cycle number(s) of the outlier(s) as a cycle number indicative of an abnormal signal.

11. The method of claim 10, wherein the ranking scores are assigned at regular intervals.

12. The method of claim 10, wherein the total ranking score in the sub-step (d-2) is obtained by summing ranking scores assigned to the same cycle number of each dataset.

13. The method of claim 10, wherein the sub-step (d-3) is performed by (i) arranging the total ranking scores at each cycle number in the order of magnitude; (ii) calculating a gap between two neighboring total ranking scores in the arrangement; (iii) identifying an outlier gap in the arrangement; and (iv) determining as an outlier(s) a total ranking score smaller than or equal to a relatively small total ranking score out of two neighboring total ranking scores of the outlier gap, or determining as an outlier(s) a total ranking score larger than or equal to a relatively large total ranking score out of two neighboring total ranking scores of the outlier gap.

14. The method of claim 13, wherein the outlier gap is (i) a gap having the largest size; (ii) one of a gap having the largest size and a gap having the second largest size; or (iii) one of gap(s) deviating from the mean gap size.

15. The method of claim 13, wherein a reference total ranking score is further used to identify an outlier gap.

16. The method of claim 15, wherein the reference total ranking score is obtained by (i) further assigning a reference ranking score to each dataset, wherein the reference ranking score is smaller than all ranking scores assigned to all cycle numbers in the sub-step (d-1) when a smaller ranking score is assigned to a cycle number having a smaller normality score in each dataset in the sub-step (d-1) or the reference ranking score is larger than all ranking scores assigned to all cycle numbers in the sub-step (d-1) when a larger ranking score is assigned to a cycle number having a smaller normality score in each dataset in the sub-step (d-1); and (ii) summing the reference ranking scores assigned to all datasets.

17. The method of claim 10, wherein the sub-step (d-3) is performed by applying a threshold to the total ranking scores and determining as an outlier(s) a total ranking score smaller than the threshold or determining as an outlier(s) a total ranking score larger than the threshold.

18. The method of claim 1, wherein the two or more datasets comprise datasets obtained by detection at different detection temperatures in a signal amplification reaction, datasets obtained by detection using different signal detection means, or a combination thereof.

19. A computer readable storage medium containing instructions to configure a processor to perform a method for detecting an abnormal signal using two or more datasets, comprising:
 (a) receiving two or more datasets by a signal amplification reaction in a single reaction vessel; wherein each of the datasets comprises a plurality of data points; wherein each of the data points has a cycle number and a signal value at the cycle number;
 (b) calculating a second-order change value at each cycle number of each dataset;
 (c) calculating a normality score at each cycle number of each dataset by using the second-order change value; wherein the calculation of the normality score is performed by a mathematical operation that represents sign change between and magnitudes of the second-order change values at two consecutive cycle numbers; and
 (d) determining a cycle number indicative of an abnormal signal by using the normality score.

* * * * *